US012730104B2

(12) United States Patent
Luo et al.

(10) Patent No.: US 12,730,104 B2
(45) Date of Patent: Sep. 8, 2026

(54) METHOD AND SYSTEM FOR DETECTING CELL-KILLING EFFICACY AND/OR IMMUNE ACTIVITY, AND APPLICATION THEREOF

(71) Applicant: SHANGHAI RUIYU BIOTECH. CO., LTD., Shanghai (CN)

(72) Inventors: Puwen Luo, Shanghai (CN); Jing Jiang, Shanghai (CN); Kai Chen, Shanghai (CN); Weiya Fan, Shanghai (CN)

(73) Assignee: SHANGHAI RUIYU BIOTECH. CO., LTD., Shanghai (CN)

( * ) Notice: Subject to any disclaimer, the term of this patent is extended or adjusted under 35 U.S.C. 154(b) by 518 days.

(21) Appl. No.: 18/301,247

(22) Filed: Apr. 16, 2023

(65) Prior Publication Data

US 2023/0273188 A1 Aug. 31, 2023

Related U.S. Application Data

(63) Continuation of application No. PCT/CN2021/127199, filed on Oct. 28, 2021.

(30) Foreign Application Priority Data

Oct. 28, 2020 (CN) ......................... 202011173457.4
Oct. 28, 2020 (CN) ......................... 202011173496.4
Oct. 28, 2020 (CN) ......................... 202011173498.3
Oct. 28, 2020 (CN) ......................... 202011173508.3
Oct. 28, 2020 (CN) ......................... 202011176203.8
Jan. 29, 2021 (CN) ......................... 202110127301.0
May 28, 2021 (CN) ......................... 202110595121.5

(51) Int. Cl.
*G01N 33/50* (2006.01)
*G06T 7/00* (2017.01)
*G06T 7/11* (2017.01)
*G06T 7/136* (2017.01)
*G06T 7/33* (2017.01)
*G06T 7/90* (2017.01)

(52) U.S. Cl.
CPC ..... *G01N 33/5047* (2013.01); *G01N 33/5011* (2013.01); *G06T 7/0014* (2013.01); *G06T 7/11* (2017.01); *G06T 7/136* (2017.01); *G06T 7/33* (2017.01); *G06T 7/90* (2017.01); *G01N 2500/10* (2013.01); *G06T 2207/10056* (2013.01); *G06T 2207/10064* (2013.01); *G06T 2207/20221* (2013.01); *G06T 2207/30024* (2013.01)

(58) Field of Classification Search
CPC ........... G01N 33/5047; G01N 2500/10; G01N 15/1433; G01N 15/1429; G01N 2015/1006; G06T 7/0014; G06T 7/11; G06T 7/136; G06T 7/33; G06T 7/90; G06T 2207/10056; G06T 2207/10064; G06T 2207/20221; G06T 2207/30024; G06T 2207/20084; G06T 7/0012
See application file for complete search history.

(56) References Cited

U.S. PATENT DOCUMENTS 5,902,733 A 5/1999 Hirt et al.
6,252,664 B1 6/2001 Barberá-Guillem
10,768,105 B1 9/2020 Mohan et al.
2002/0146746 A1* 10/2002 Nixon ................. G01N 33/582 435/40.5
2003/0003101 A1 1/2003 Bander
2010/0232675 A1 9/2010 Ortyn et al.
2011/0183370 A1 7/2011 Noiseux et al.
2011/0254943 A1 10/2011 Ozinsky et al.
2012/0140991 A1 6/2012 Nakajima et al.
2012/0200694 A1 8/2012 Garsha et al.
2012/0302462 A1 11/2012 Onfelt et al.
(Continued)

FOREIGN PATENT DOCUMENTS

CN 101149327 A 3/2008
CN 101650364 A 2/2010
(Continued)

OTHER PUBLICATIONS

Arteta, C et al. Detecting overlapping instances in microscopy images using external region trees. Medical Image Analysis. 2016. 27: 3-16. (Year: 2016).*

(Continued)

*Primary Examiner* — David W Berke-Schlessel
*Assistant Examiner* — Susan E. Fernandez
(74) *Attorney, Agent, or Firm* — METIS IP LLC

(57) ABSTRACT

The embodiments of the present disclosure provide a method, a system, and an application for detecting at least one of a cell-killing efficacy or an immune activity. The method comprises: obtaining a plurality of microscopic images of a fixed area of a co-culture sample, wherein the co-culture sample is a cell sample obtained by co-culturing target cells and effector cells, the fixed area of the co-culture sample includes a plurality of objects, wherein the plurality of objects are a cell group including cells with different properties, each of the plurality of objects having an image-identifiable feature; performing an image overlapping synthesis analysis or an image fusion analysis for the plurality of microscopic images to obtain the cell properties of the plurality of objects and make statistics to cell parameters associated with the cell properties; and evaluating at least one of the cell-killing efficacy or the immune activity of the effector cells based on the cell parameters.

18 Claims, 9 Drawing Sheets

(56) References Cited

U.S. PATENT DOCUMENTS

| | | | | |
|---|---|---|---|---|
| 2013/0011394 | A1 | 1/2013 | Knoetgen | |
| 2013/0027539 | A1 | 1/2013 | Kiyota et al. | |
| 2015/0055886 | A1* | 2/2015 | Oh | H04N 23/11 382/284 |
| 2015/0071927 | A1* | 3/2015 | Zhang | A61P 35/00 536/23.53 |
| 2015/0132766 | A1 | 5/2015 | Yasuda et al. | |
| 2015/0301046 | A1 | 10/2015 | Schmidt et al. | |
| 2016/0206660 | A1 | 7/2016 | Shi et al. | |
| 2017/0042939 | A1* | 2/2017 | Zhang | A61K 40/4271 |
| 2017/0052356 | A1 | 2/2017 | Lei et al. | |
| 2017/0315129 | A1 | 11/2017 | Yamada et al. | |
| 2018/0017492 | A1 | 1/2018 | Kato et al. | |
| 2018/0051317 | A1 | 2/2018 | Bonnaudet et al. | |
| 2018/0074045 | A1 | 3/2018 | Ballan | |
| 2019/0302000 | A1 | 10/2019 | Lo et al. | |
| 2020/0102537 | A1 | 4/2020 | Jiao et al. | |
| 2020/0141856 | A1 | 5/2020 | Yan et al. | |
| 2022/0020134 | A1 | 1/2022 | Kou et al. | |
| 2023/0142803 | A1 | 5/2023 | Zhang et al. | |

FOREIGN PATENT DOCUMENTS

| | | | | |
|---|---|---|---|---|
| CN | 102127587 | A | 7/2011 | |
| CN | 102719399 | A | 10/2012 | |
| CN | 103045712 | A | 4/2013 | |
| CN | 103712967 | A | 4/2014 | |
| CN | 104266955 | A | 1/2015 | |
| CN | 104894072 | A | 9/2015 | |
| CN | 105445171 | A | 3/2016 | |
| CN | 105606581 | A | 5/2016 | |
| CN | 106085416 | A | 11/2016 | |
| CN | 106203450 | A | 12/2016 | |
| CN | 206132818 | U | 4/2017 | |
| CN | 107064085 | A | 8/2017 | |
| CN | 107686859 | A | 2/2018 | |
| CN | 107760754 | A | 3/2018 | |
| CN | 108558990 | A | 9/2018 | |
| CN | 108753916 | A | 11/2018 | |
| CN | 108921172 | A | 11/2018 | |
| CN | 110093326 | A | 8/2019 | |
| CN | 110231275 | A | 9/2019 | |
| CN | 110354142 | A | 10/2019 | |
| CN | 110358805 | A | 10/2019 | |
| CN | 110402853 | A | 11/2019 | |
| CN | 110991379 | A | 4/2020 | |
| CN | 111041064 | A | 4/2020 | |
| CN | 111062871 | A | 4/2020 | |
| CN | 210401827 | U | 4/2020 | |
| CN | 111235209 | A | 6/2020 | |
| CN | 111239995 | A | 6/2020 | |
| CN | 210775221 | U | 6/2020 | |
| CN | 111398237 | A | 7/2020 | |
| CN | 112285081 | A | 1/2021 | |
| CN | 112285082 | A | 1/2021 | |
| CN | 112285083 | A | 1/2021 | |
| CN | 212364081 | U | 1/2021 | |
| CN | 112301086 | A | 2/2021 | |
| CN | 112304851 | A | 2/2021 | |
| CN | 112813133 | A | 5/2021 | |
| EP | 1316793 | A1 | 6/2003 | |
| EP | 1233058 | B1 | 12/2006 | |
| WO | WO-2020081340 | A1 * | 4/2020 | G06T 7/0012 |

OTHER PUBLICATIONS

Abhinav, K et al. Image segmentation of multi-shaped overlapping objects. Proceedings of the 13th International Joint Conference on Computer Vision, Imaging and Computer Graphics Theory and Applications (VISIGRAPP 2018). 2018. 4: 410-418. (Year: 2018).*

Ambikumar, A et al. Extending the depth of field in microscopy: a review. 2016 International Conference on Image and Vision Computing New Zealand (IVCNZ), Palmerston North, New Zealand. 2016. 6 pages. (Year: 2016).*

Kan, A. Machine learning applications in cell image analysis. Immunology and Cell Biology. 2017. 95: 525-530. (Year: 2017).*

The Extended European Search Report in European Application No. 21885279.6 mailed on Mar. 6, 2024, 9 pages.

International Search Report in PCT/CN2021/127199 mailed on Jan. 19, 2022, 7 pages.

Written Opinion in PCT/CN2021/127199 mailed on Jan. 19, 2022, 8 pages.

First Office Action in Chinese Application No. 202011173496.4 mailed on Mar. 30, 2021, 15 pages.

The Second Office Action in Chinese Application No. 202011173496.4 mailed on Jun. 16, 2021, 15 pages.

First Office Action in Chinese Application No. 202011173508.3 mailed on Apr. 16, 2021, 18 pages.

First Office Action in Chinese Application No. 202011178203.8 mailed on Mar. 30, 2021, 17 pages.

First Office Action in Chinese Application No. 202011173498.3 mailed on Mar. 31, 2021, 14 pages.

First Office Action in Chinese Application No. 202110127301.0 mailed on Mar. 2, 2022, 20 pages.

First Office Action in Chinese Application No. 202110595121.5 mailed on Jan. 29, 2022, 23 pages.

The Second Office Action in Chinese Application No. 202110595121.5 mailed on Apr. 20, 2022, 27 pages.

Guo, Jiqiang et al., Comparison of Ex Vivo Expanded and Highly Purified NK Cell-Mediated Cytotoxicity Detected by 3 Different Staining Methods of Flow Cytometry, Journal of Experimental Hematology, 24(6): 1691-1697, 2016.

Zhong, Xiaosong et al., A New Approach for Measurement of TIL Cytotoxicity Using Apoptosis Fluorescence Staining Assay, Shanghai Med. J., 20(12): 705-708, 1997.

Tang, Baoding, Modern Biological Technology and Exploratory Experiment, University of Science and Technology of China Press, 2015, 12 pages.

Zhuang, Ran et al., Establishment of a Method for Detecting the Level of Cell Killing Based on Cfse/Pi Double Labeling Method, The Fifth National Congress and Academic Conference of The Chinese Society of Immunology, 2006, 3 pages.

Fu, Xiaolan et al., Measurement of in Vivo Cytotoxicity by Flow Cytometry, Immunological Journal, 24(3): 350-351,355, 2008.

Pang, Aimei et al., Laboratory Technology and Clinical Diagnosis, Jilin Science and Technology Publishing House, 2017, 20 pages.

Ouyang, Weiming, Study on the Distribution, Function and its Mechanism of 9.1C3 Molecule, a Novel NK Cell Inhibitory Receptor, China Doctoral Dissertations Full-text Database Medicine and Health Science and Technology Series, 2007, 88 pages.

Chen, Bicheng et al., Two Fluorescent Dyes,—CFSE and Propidium Iodide, Were Used to Detect the Cytoxicity, Chinese Journal of Microbiology and Immunology, 2006, 2 pages.

Uploaded by SOEWR, NK Killing Experiment, Doubleday Library, 2016, 45 pages.

Xiao, Jing et al., Modern Medicine Test Technology, Tianjin Science and Technology Press, 2018, 10 pages.

He, Yong et al., Biological 3D Printing: From Medical AIDS Manufacturing to Cellular Printing,Science and Technology Press, 2019, 44 pages.

Yang, Lujing et al., Intelligent Image Processing and Application, Beijing: China Railway Publishing House, 2019, 10 pages.

Zhou, Hao et al., CFSE and PI Two Fluorochrome Stain Assay for Detecting Cytotoxicity, Journal of Practical Medicine, 24(15): 2565-2567, 2008.

* cited by examiner

Figure 2:
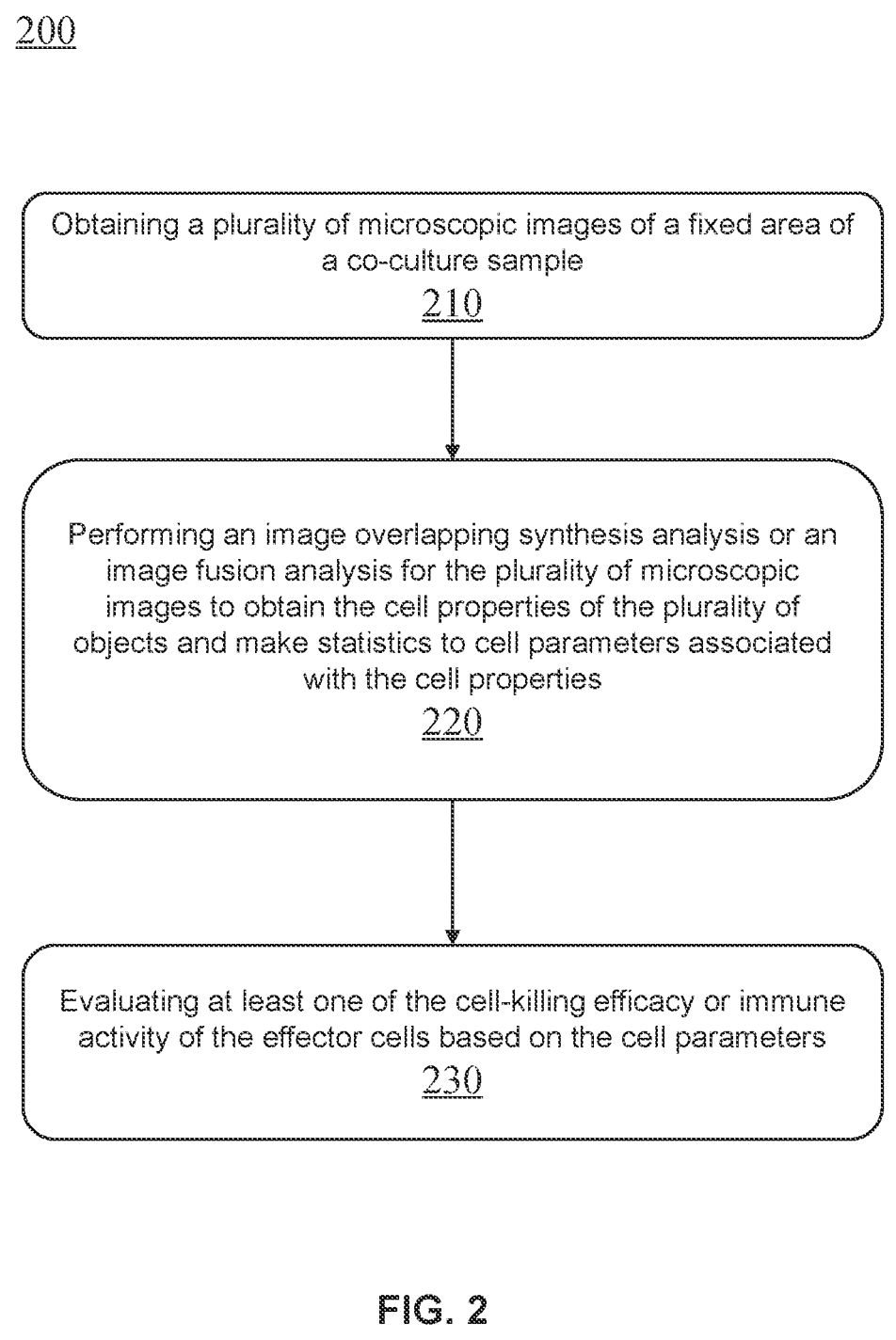

200

Obtaining a plurality of microscopic images of a fixed area of a co-culture sample
210

Performing an image overlapping synthesis analysis or an image fusion analysis for the plurality of microscopic images to obtain the cell properties of the plurality of objects and make statistics to cell parameters associated with the cell properties
220

Evaluating at least one of the cell-killing efficacy or immune activity of the effector cells based on the cell parameters
230

Figure 3:
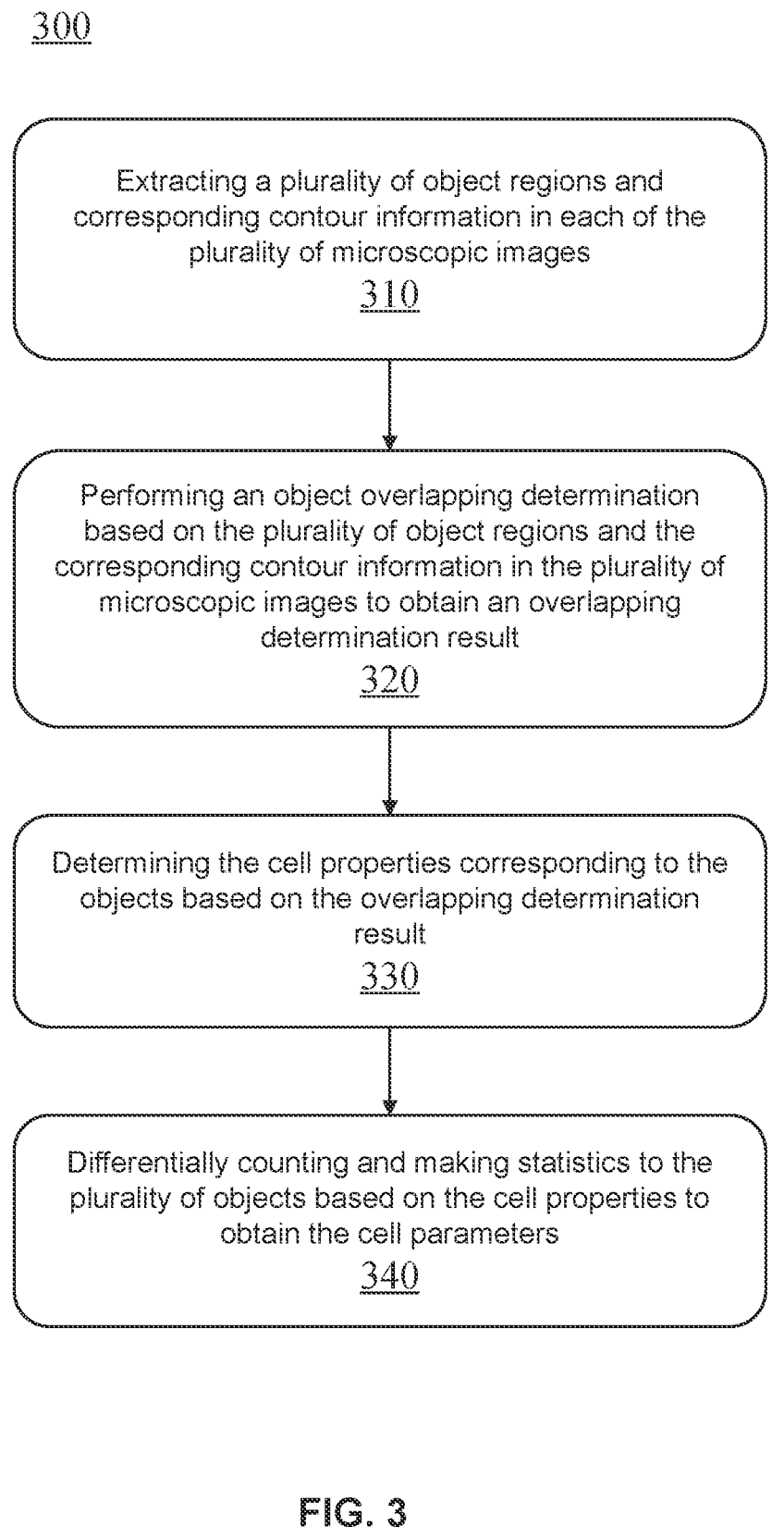

Extracting a plurality of object regions and corresponding contour information in each of the plurality of microscopic images
310

Performing an object overlapping determination based on the plurality of object regions and the corresponding contour information in the plurality of microscopic images to obtain an overlapping determination result
320

Determining the cell properties corresponding to the objects based on the overlapping determination result
330

Differentially counting and making statistics to the plurality of objects based on the cell properties to obtain the cell parameters
340

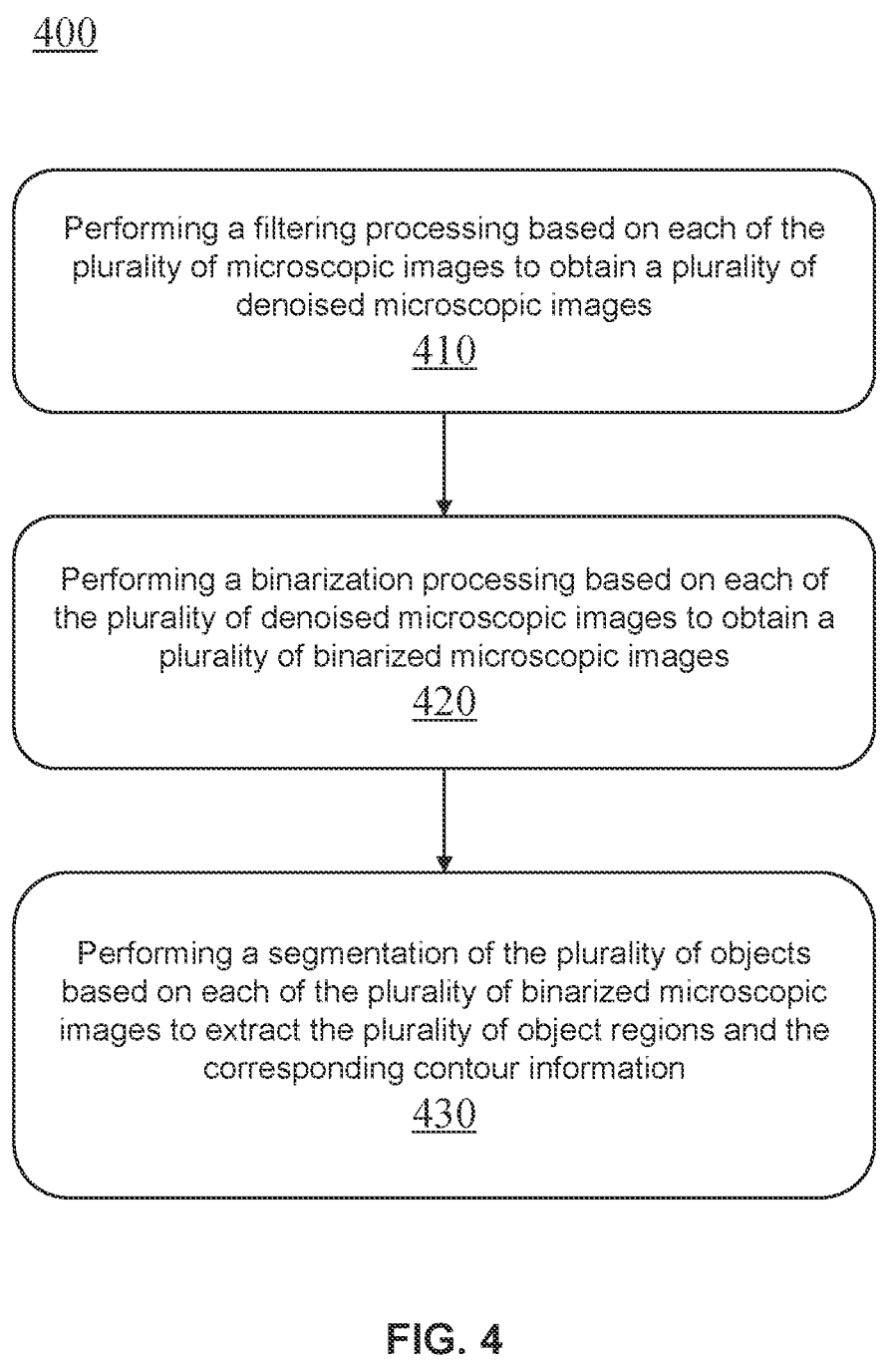

Performing a filtering processing based on each of the plurality of microscopic images to obtain a plurality of denoised microscopic images
410

Performing a binarization processing based on each of the plurality of denoised microscopic images to obtain a plurality of binarized microscopic images
420

Performing a segmentation of the plurality of objects based on each of the plurality of binarized microscopic images to extract the plurality of object regions and the corresponding contour information
430

FIG. 4

METHOD AND SYSTEM FOR DETECTING CELL-KILLING EFFICACY AND/OR IMMUNE ACTIVITY, AND APPLICATION THEREOF

CROSS-REFERENCE TO RELATED APPLICATIONS

This application is a continuation of International Application No. PCT/CN2021/127199, filed on Oct. 28, 2021, which claims priority of Chinese Patent Application No. CN202011173496.4, filed on Oct. 28, 2020, Chinese Patent Application No. CN202011173508.3, filed on Oct. 28, 2020, Chinese Patent Application No. CN202011176203.8, filed on Oct. 28, 2020, Chinese Patent Application No. CN202011173498.3, filed on Oct. 28, 2020, Chinese Patent Application No. CN202011173457.4, filed on Oct. 28, 2020, Chinese Patent Application No. CN202110127301.0, filed on Jan. 29, 2021, and Chinese Patent Application No. CN202110595121.5, filed on May 28, 2021, the entire contents of each of which are incorporated herein by reference.

TECHNICAL FIELD

The present disclosure generally relates to the field of image processing, and in particular, to a method, a system, and an application for detecting at least one of a cell-killing efficacy or an immune activity.

BACKGROUND

The detection of the cell-killing efficacy is of great significance for the quality control of immune cell therapy products. Due to the large individual differences in origins of immune cell therapy products, the low degree of large-scale preparation processes, and the fact that most of the preparations are living cell products and that the mechanism is not very clear, etc., this type of products have characteristics such as a poor uniformity of the products, limited batches, a short effective period, and a poor comparability. Thus, the quality control research of immune cell therapy products is relatively complicated, and the quality control of the killing efficacy is one of the difficulties.

Common methods for detecting the cell-killing efficacy, such as a cadmium-51 release experiment, a lactate dehydrogenase (LDH) release method, a BATDA method, a CAM method, a CytoTox-Glo method, a PKH method, a flow cytometry (FCM), etc., have many application limitations, and it is hard to balance the intuitiveness, accuracy, and efficiency. Therefore, the development of an intuitive, accurate, and efficient method for detecting at least one of the cell-killing efficacy or the immune activity has positive significance in the research and preparation of the immune cell therapy products.

SUMMARY

One of the embodiments of the present disclosure provides a method for detecting at least one of a cell-killing efficacy or an immune activity, comprising: obtaining a plurality of microscopic images of a fixed area of a co-culture sample, wherein the co-culture sample is a cell sample obtained by co-culturing target cells and effector cells, the fixed area of the co-culture sample includes a plurality of objects, wherein the plurality of objects are a cell group including cells with different properties, each of the plurality of objects having an image-identifiable feature, and a cell property of each of the plurality of objects being characterized by a collection of feature information of the image-identifiable feature of the object displayed in the plurality of microscopic images; performing an image overlapping synthesis analysis or an image fusion analysis for the plurality of microscopic images to obtain the cell properties of the plurality of objects and make statistics to cell parameters associated with the cell properties; and evaluating at least one of the cell-killing efficacy or the immune activity of the effector cells based on the cell parameters.

One of the embodiments of the present disclosure provides a system for detecting at least one of a cell-killing efficacy or an immune activity, comprising following modules: a microscopic imaging module, configured to obtain a plurality of microscopic images of a fixed area of a co-culture sample, wherein the co-culture sample is a cell sample obtained by co-culturing target cells and effector cells, the fixed area of the co-culture sample includes a plurality of objects, wherein the plurality of objects are a cell group including cells with different properties, each of the plurality of objects having an image-identifiable feature, and a cell property of each of the plurality of objects being characterized by a collection of feature information of the image-identifiable feature of the object displayed in the plurality of microscopic images; an image analysis module, configured to perform an image overlapping synthesis analysis or an image fusion analysis for the plurality of microscopic images to obtain the cell properties of the plurality of objects and make statistics to cell parameters associated with the cell properties; and an evaluation module, configured to evaluating at least one of the cell-killing efficacy or the immune activity of the effector cells based on the cell parameters.

One of the embodiments of the present disclosure provides a device for detecting at least one of a cell-killing efficacy or an immune activity. The device includes a processor configured to implement the method of detecting at least one of a cell-killing efficacy or an immune activity.

One of the embodiments of the present disclosure provides a computer-readable storage medium. The storage medium stores computer instructions, and after the computer reads the computer instructions in the storage medium, the computer executes a method for detecting at least one of the cell-killing efficacy or the immune activity.

One of the embodiments of the present disclosure provides an application of a method or system in detecting the cell-killing efficacy, detecting the immune activity of the effector cells, preparing immune products, a quality control of the immune products, or an evaluation of an individual immune function.

BRIEF DESCRIPTION OF THE DRAWINGS

The present disclosure will be further described in the form of exemplary embodiments, which will be described in detail by the accompanying drawings. These embodiments are not limited, in these embodiments, the same numbers refer to the same structures, wherein:

FIG. 2 is a flowchart illustrating an exemplary process for detecting at least one of the cell-killing efficacy or the immune activity according to some embodiments of the present disclosure;

FIG. 3 is a flowchart illustrating an exemplary process for performing the image overlapping synthesis analysis on a plurality of microscopic images according to some embodiments of the present disclosure;

FIG. 4 is a flowchart illustrating an exemplary process for extracting contours of objects in the microscopic images according to some embodiments of the present disclosure;

DETAILED DESCRIPTION

Figure 1:
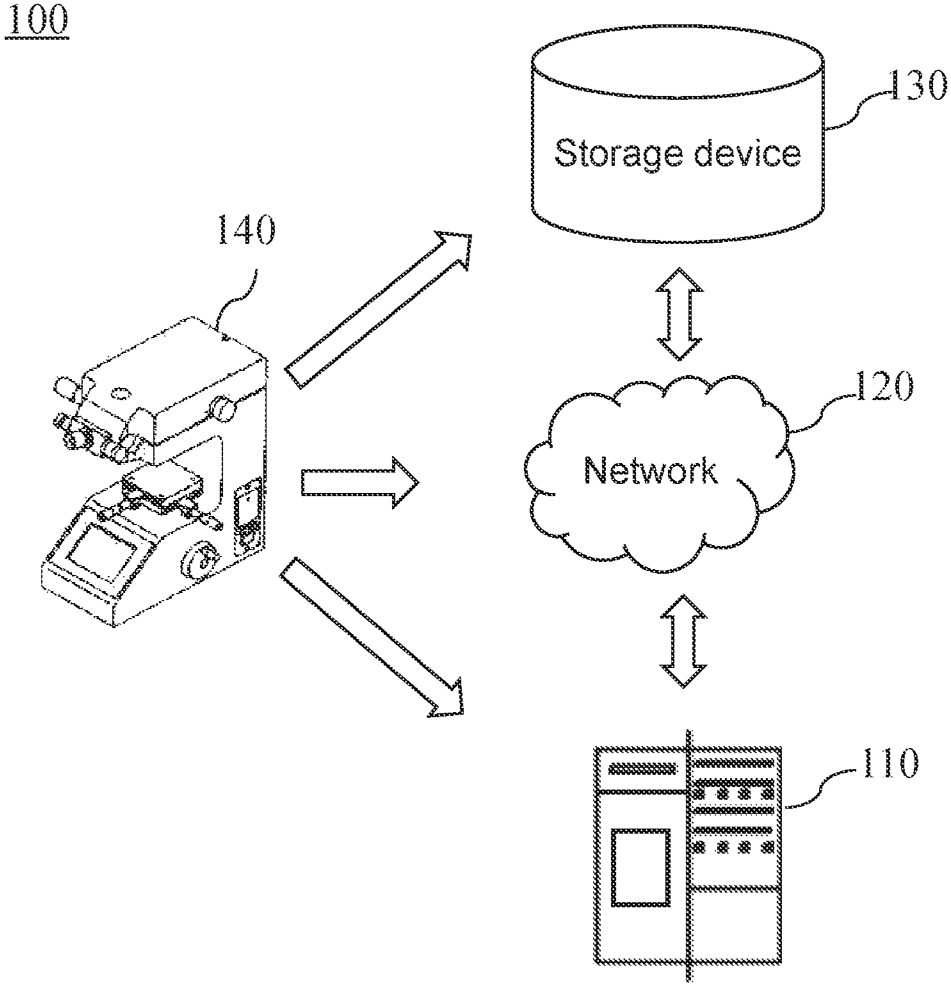
FIG. 1 is a schematic diagram of an application scenario of a system for detecting at least one of a cell-killing efficacy or an immune activity according to some embodiments of the present disclosure.

In order to more clearly illustrate the technical solutions of the embodiments of the present disclosure, the following contents will briefly introduce the drawings that need to be used in the description of the embodiments. Obviously, the drawings in the following description are only some examples or embodiments of the present disclosure, and those skilled in the art, without creative efforts, may apply the present disclosure to other similar situations according to these drawings. Unless obviously obtained from the context or the context illustrates otherwise, the same numeral in the drawings refers to the same structure or operation.

It is to be understood that "system," "device," "unit" and/or "module" as used herein is a manner used to distinguish different components, elements, members, parts, or assemblies at different levels. However, if other words may achieve the same purpose, the words may be replaced by other expressions.

As shown in the present disclosure and the claims, unless the context clearly suggests exceptional circumstances, the words "a," "an," "and/or," and "the" do not specifically refer to the singular form, but may also include the plural form. Generally speaking, the terms "comprise" and "include" only imply that the clearly identified operations and elements are included, and these operations and elements do not constitute an exclusive list, and the methods or the devices may also include other operations or elements.

The flowcharts used in the present disclosure illustrate operations that the system implements according to some embodiments of the present disclosure. It should be understood that the previous or back operations may not be accurately implemented in order. Instead, the various operations may be processed in reverse order or simultaneously. At the same time, other operations may also be added to these processes, or a certain operation or several operations may be removed from these processes.

FIG. 1 is a schematic diagram of the application scenario of a system for detecting at least one of a cell-killing efficacy or an immune activity according to some embodiments of the present disclosure.

As shown in FIG. 1, a detection system 100 may include a server 110, a network 120, a storage device 130, and an image acquisition device 140.

The server 110 may be configured to manage resources and process at least one of data or information from at least one component of the detection system 100 or an external data source (e.g., a cloud data center). For example, the image overlapping synthesis analysis may be performed for a plurality of microscopic images (bright-field microscopic images and at least one fluorescence microscopic image). As another example, the image fusion analysis may be performed for the plurality of microscopic images. During the processing process, the server 110 may obtain data (e.g., one or more of the plurality of microscopic images) from the storage device 130 or save data (e.g., cell properties and cell parameters of objects,) to the storage device 130, and also may read data (e.g., at least one of the bright-field microscopic images or at least one fluorescence microscopic image) from other sources, such as the image acquisition device 140, via the network 120.

In some embodiments, the server 110 may be a single server or a server group. The server group may be centralized or distributed (e.g., the server 110 may be a distributed system), dedicated, or concurrently provided by other devices or systems. In some embodiments, the server 110 may be regional or remote. In some embodiments, the server 110 may be implemented on a cloud platform or provided in a virtual fashion. As an example, the cloud platform may include private clouds, public clouds, hybrid clouds, community clouds, distributed clouds, internal clouds, multilayer clouds, or the like, or any combination thereof.

In some embodiments, the server 110 may include processing devices. The processing devices may process at least one of the data or information obtained from other devices or system components. A processor may execute program instructions based on at least one of such data, information, or processing results to perform one or more of the functions described in the present disclosure. In some embodiments, the processing devices may include one or more sub-processing devices (e.g., a single-core processing device or a multi-core and multi-core processing device). As an example, the processing device may include central processing units (CPU), application-specific integrated circuits (ASIC), application-specific instruction processors (ASIP), graphics processors (GPU), physical processors (PPU), digital signal processors (DSP), field-programmable gate arrays (FPGA), programmable logic circuits (PLD), controllers, microcontroller units, reduced instruction set computers (RISC), microprocessors, or the like, or any combination of the above.

The network 120 may connect various components of the detection system 100 and/or connect the system to external resource components. The network 120 enables communication between the various components and with other components outside the system, facilitating at least one of the exchange of data or the exchange of information. In some embodiments, the network 120 may be any one or more of a wired network or a wireless network. For example, network 120 may include cable networks, fiber optic networks, telecommunications networks, Internet, LAN (LAN), WAN (WAN), Wireless LAN (WLAN), Urban Domain Network (MAN), and Public Exchange Phone Network (PSTN) (PSTN), Bluetooth Network, ZigBee (Zig- Bee), near-field communication (NFC), internal bus, inner lines, cable connections, etc. or arbitrary combinations. For example, the network 120 may include cable networks, fiber optic networks, telecommunications networks, the Internet, local area networks (LAN), wide area networks (WAN), wireless local area networks (WLAN), metropolitan area networks (MAN), public switched telephone networks (PSTN), Bluetooth networks, ZigBee networks (ZigBee), near field communication (NFC), in-device bus, in-device lines, cable connections, or the like, or any combination thereof. The network connection between the various components may be in one of the above-mentioned ways, and may also be in a variety of ways. In some embodiments, the network may be in point-to-point, shared, centralized, etc., various topologies or a combination of a plurality of topologies. In some embodiments, the network 120 may include one or more network access points. For example, the network 120 may include wired or wireless network access points, such as at least one of base stations or network exchange points, through which one or more components of the detection system 100 may connect to the network 120 to exchange at least one of data or information.

The storage device 130 may be used to store at least one of data (e.g., the bright-field microscopic images and at least one fluorescence microscopic image) or instructions. The storage device 130 is implemented in a single central server, a plurality of servers connected by communication links, or a plurality of personal devices. In some embodiments, the storage device 130 may include mass memories, removable memories, volatile read-write memories (e.g., random access memories RAM), read-only memories (ROM), or the like, or any combination thereof. Illustratively, the mass memories may include magnetic disks, optical disks, solid-state disks, or the like. In some embodiments, the storage device 130 may be implemented on the cloud platform.

The image acquisition device 140 may be configured to obtain a plurality of microscopic images of a fixed area of a co-culture sample (the bright-field microscopic images and at least one fluorescence microscopic image). In some embodiments, the image acquisition device that obtains the different microscopic images (the bright-field microscopic image and at least one fluorescence microscopic image) may be the same. For example, the image acquisition device 140 may be a metallographic microscope. In some embodiments, the image acquisition devices that obtain different microscopic images may be different. For example, the image acquisition device 140 may include a bright-field microscope for obtaining the bright-field microscopic images and a fluorescence microscope for obtaining at least one fluorescence microscopic image.

In some embodiments, the detection system 100 may also include a terminal device (not shown). The terminal device may include at least one of input devices (e.g., keyboards, mice) or output devices (e.g., display screens, speakers). Users may interact with the processing device 110, the image acquisition device 140 and other devices through the terminal device. For example, the users may check the microscopic images obtained by the image acquisition device 140 through the terminal device. For another example, the users may directly observe the image analysis result processed by the processing device through the terminal device.

In some embodiments, the detection system 100 may include a microscopic imaging module, an image analysis module, and an evaluation module.

The microscopic imaging module may be configured to obtain microscopic images of cell samples. The microscopic images may include the bright-field microscopic images and at least one fluorescence microscopic image. In some embodiments, the cell samples may include a co-culture sample and a control group sample. The co-culture sample is a cell sample obtained by co-culturing target cells and effector cells. The control group sample is a cell sample obtained by culturing at least one of the target cells or effector cells alone.

For more description of the microscopic imaging module, reference may be made to operation 210, which will not be repeated here.

The image analysis module may be configured to perform the image overlapping synthesis analysis for the plurality of microscopic images to obtain the cell properties of the plurality of objects, and make statistics to cell parameters associated with the cell properties. Further, in some embodiments, the image analysis module may extract the plurality of object regions and the corresponding contour information in each of the microscopic images. The object region is an image region containing a single object with a closed contour. In some embodiments, the image analysis module may perform an object overlapping determination based on the object regions and the corresponding contour information in a plurality of microscopic images to obtain an overlapping determination result. In some embodiments, the image analysis module may obtain the cell properties corresponding to the objects based on the overlapping determination result.

In some embodiments, the image analysis module may differentially count and make statistics to the plurality of objects based on the cell properties to obtain the cell parameters.

The image analysis module may also be configured to perform the image fusion analysis for the plurality of microscopic images to obtain the cell properties of the plurality of objects, and make statistics to cell parameters associated with the cell properties.

In some embodiments, the image analysis module may obtain a fused image based on the plurality of microscopic images. Further, in some embodiments, the image analysis module may extract feature points of each of the microscopic images. In some embodiments, the image analysis module may register the plurality of microscopic images based on corresponding feature points of the plurality of microscopic images. In some embodiments, the image analysis module may obtain the fused image based on fusing the registered plurality of microscopic images based on at least one of transparency or chroma.

In some embodiments, the image analysis module may analyze the fused image to obtain the cell properties of the plurality of objects and make statistics to cell parameters associated with the cell properties. Further, in some embodiments, the image analysis module may obtain a plurality of object image blocks based on the fused image. The object image block is an image block containing a single object. In some embodiments, the image analysis module may extract color features and shape features of the plurality of object image blocks. In some embodiments, the image analysis module may obtain the cell properties of the plurality of objects and make statistics to cell parameters associated with the cell properties of the plurality of objects based on the color features and the shape features of the plurality of object image blocks.

In some embodiments, the image analysis module may also process the fused image based on an image recognition model to obtain the cell properties of the plurality of objects, and make statistics to the cell parameters associated with the cell properties. In some embodiments, the image recognition model may be a machine-learning model.

The evaluation module may be configured to evaluate at least one of the cell-killing efficacy or the immune activity of the effector cells based on the cell parameters. In some embodiments, the evaluation module may evaluate at least one of the cell-killing efficacy or the immune activity of the effector cells based on one or more of a death rate of the target cells, a cell-specific killing rate, and a self-injury rate of the effector cells among the cell parameters.

In some embodiments, the detection system 100 may also include a sample stage module and an automatic sample replacement module.

The sample stage module may be configured to carry cell culture plates. The cell culture plate having a plurality of sample holes is configured to carry the co-culture sample with at least two effect-target ratios, and the microscopic imaging module images the fixed area of the co-culture sample in each sample hole of the cell culture plates respectively, so as to obtain a plurality of microscopic images of the fixed area of the co-culture samples.

The automatic sample replacement module may be configured to replace cell culture plates. The microscopic imaging module images the fixed area of the co-culture samples on the replaced cell culture plates respectively and obtains a plurality of microscopic images of the fixed area on the replaced cell culture plates.

It should be noted that the above description of the detection system and its modules are only for the convenience of description, and does not limit the present disclosure to the scope of the illustrated embodiments. It will be understood that for those skilled in the art, after understanding the principle of the system, it is possible to arbitrarily combine various modules, or form subsystems to connect with other modules without departing from this principle. In some embodiments, the microscopic imaging module, the image analysis module, and the evaluation module disclosed in FIG. 1 may be different modules in a system or may be one module that implements the functions of the above two or more modules. For example, the microscopic imaging module and a fluorescence microscopic imaging module may be the same module, which may obtain both the bright-field microscopic images of the co-culture samples and the fluorescence microscopic images of the co-culture samples. For example, each module may share one storage module, and each module may also have its own storage module. Such deformations may be all within the scope of the protection of the present disclosure.

FIG. 2 is a flowchart illustrating an exemplary process for detecting at least one of the cell-killing efficacy or the immune activity according to some embodiments of the present disclosure. As shown in FIG. 2, process 200 includes operations 210 to 230.

Operation 210 is the operation of obtaining the microscopic images. In operation 210, a plurality of microscopic images of a fixed area of the co-culture sample may be obtained. In some embodiments, the microscopic imaging module may perform operation 210. In some embodiments, the microscopic imaging module may obtain the plurality of microscopic images through the image acquisition device 140. In some embodiments, the microscopic imaging module may obtain a plurality of pre-acquired microscopic images from the storage device 130 via the network 120.

The co-culture sample is a cell sample obtained by co-culturing target cells and effector cells. The fixed area of the co-culture sample includes a plurality of objects, and the plurality of objects are a cell group comprising cells with different properties. Each of the plurality of objects has at least one image-identifiable feature, and a cell property of each of the plurality of objects are characterized by a collection of feature information displayed in the plurality of microscopic images based on the image-identifiable features of the object. In some embodiments, the fixed area may be an entire image acquisition area of the co-culture sample that includes all the objects. In some embodiments, the fixed area may be a portion of the image acquisition area of the co-culture sample that includes a portion of the objects.

The target cells refer to various tumor cells or virus-infected cells corresponding to immune cells. In some embodiments, the target cells are at least one of the virus-infected cells or the tumor cells. The tumor cells and the virus-infected cells that may be used as the target cells include, but are not limited to, K562 cells, Daudi cells, Jurkat cells, MCF-7 cells, A549 cells, HepG2 cells, or the like.

The effector cells refer to immune cells or engineered cells that participate in removing foreign antigens and performing effector functions in an immune response. In some embodiments, the effector cells are at least one of the immune cells or the engineered cells. The immune cells and the engineered cells that may be used as the effector cells include, but are not limited to, PBMC cells, NK cells, T cells, CTL cells, LAK cells, CIK cells, TIL cells, DC cells, CAR-T cells, CAR-NK cells, NK92MI-CD16a cells, or the like.

The cell properties may be the manifestation of one or more of a series of cell life phenomena (such as the growth, the development, the proliferation, the differentiation, the inheritance, the metabolism, the stress, the movement, the aging, and the death). In some embodiments, the cell properties may include a cell type and a cell survival status. For example, the cell type may include the target cells and the effector cells; the cell survival status may include living cells and dead cells. The living cells are cells that may carry out metabolism, reproduction, and replication, and are mainly characterized by a complete cell membrane and selective permeability. The dead cells are cells that cannot normally perform biological functions, metabolism, reproduction, and replication, mainly characterized by cell membrane damage and loss of selective permeability. According to different cell death methods, it may include dead cells produced by cell death processes such as apoptosis and necrosis, ferroptosis, pyroptosis, and autophagy. As another example, the cell type may include target cells, effector cells, cell debris, and impurities; the cell survival status may include living cells, apoptotic cells, and necrotic cells. The apoptotic cells are cells that die autonomously and orderly under the control of genes in order to maintain the stability of the internal environment. The necrotic cells are cells that have been damaged and died by extreme physical factors, chemical factors or severe pathological stimuli. In some embodiments, the plurality of objects within the fixed area are a cell group of living target cells, dead target cells, living effector cells, and dead effector cells.

Objects with different cell properties have different image-identifiable features so that the cell properties of the objects are characterized by the image-identifiable features. The image-identifiable features of the objects may have many different specific types, and different microscopic image combinations are used to perform image analysis on the different types of image-identifiable features.

In some embodiments, the image-identifiable features include fluorescent label features. When it is determined that the cell property of each object in the fixed area is one of the living target cells, the dead target cells, the living effector cells and the dead effector cells, the cell properties of the object may be characterized by different fluorescent label combinations.

In some embodiments, the cell properties of the object are characterized by a combination of three fluorescent labels. Specifically, the co-culture sample is obtained by labeling the cells with three fluorescent labels, and the operations of obtaining the co-culture sample include: obtaining the co-culture product based on the co-culture of the target cells carrying a preset fluorescent label and the effector cells without fluorescent labels; labeling the co-culture product with the total cell fluorescent label and the dead cell fluorescent label respectively after co-culturing the co-culture product for a predetermined time to obtain the co-culture sample; The image-identifiable features characterizing the cell properties of the objects are specifically: in the fixed area of the co-culture sample, the objects carrying the preset fluorescent label and the total cell fluorescent label are the living target cells, the objects carrying the preset fluorescent label, the total cell fluorescent label and the dead cell fluorescent label are the dead target cells, and the objects that only carrying the total cell fluorescent label are the living effector cells, the objects carrying the total cell fluorescent label and the dead cell fluorescent label are the dead effector cells.

The preset fluorescent label is used to label target cells before co-culture. In some embodiments, the preset fluorescent labels may be fluorescent proteins or cell dyes. In some embodiments, preferably, the fluorescent protein that may be used as the preset fluorescent label are green fluorescent proteins (GFP) or red fluorescent proteins (RFP). In some embodiments, preferably, the cell dyes that may be used as the preset fluorescent label is carboxyfluorescein diacetate succinimidyl ester (CFSE) or calcein-AM (Calcein-AM). It should be noted that for target cells labeled with cell dyes that are prone to background fluorescence, the target cells need to be washed before co-culture product with the effector cells.

The total cell fluorescent label may be used to label all cells in the co-culture sample. In some embodiments, the total cell fluorescent label may be nuclear dyes. The nuclear dyes that may be used as the total cell fluorescent label include, but are not limited to, Hoechst33342, DAPI, or the like.

The dead cell fluorescent label may only label the dead cells in the co-culture sample. The dead cell fluorescent label may be any dead cell label dye. The dead cell label dye that may be used as the dead cell fluorescent label includes, but is not limited to, Annexin-V (Annexin-V), SYTOX Green cyanine (SYTOX Green), propidium bromide (PI), 7-aminoactinomycin D (7-AAD), or the like.

In some embodiments, the cell properties of the object are characterized by a combination of two fluorescent labels. Specifically, the co-culture sample is obtained by labeling the sample with two fluorescent labels, and the operation of obtaining the co-culture sample includes: obtaining the co-culture product based on the co-culture of the target cells carrying preset fluorescent label and the effector cells without fluorescent labels; labeling the co-culture product with the dead cell fluorescent label after co-culturing for a predetermined time to obtain the co-culture sample. The image-identifiable features characterizing the cell properties of the objects are specifically: in the fixed area of the co-culture sample, the objects that only carry the preset fluorescent label are the living target cells, the objects carrying the preset fluorescent label and the dead cell fluorescent label are the dead target cells, and the objects not carrying the fluorescent label are the effector cells, the objects that only carrying the dead cell fluorescent label are the dead effector cells.

In some embodiments, the image-identifiable features include fluorescent label features and cell diameter features. When it is determined that the cell property of each object in the fixed area is one of the living target cells, the dead target cells, the living effector cells and the dead effector cells, the cell properties of the object may be characterized by different combinations of the fluorescent label features and the cell diameter features.

In some embodiments, the cell properties of the object are characterized by a combination of the fluorescent label and effector/target cell diameter. Specifically, the co-culture sample is obtained by labeling the cells with a fluorescent label, and the operation of obtaining the co-culture sample includes: obtaining the co-culture product based on the co-culture of the target cells without fluorescent labels and the effector cells without fluorescent labels; marking the co-culture product with the dead cell fluorescent label after co-culturing for a predetermined time to obtain the co-culture sample. The image-identifiable features characterizing the cell properties of the objects are specifically: in the fixed area of the co-culture sample, the objects without fluorescent labels and having a diameter greater than or equal to the minimum diameter of the target cell are the living target cells, the objects carrying the dead cell fluorescent label and having a diameter greater than or equal to the minimum diameter of the target cell are the dead target cells, the objects without fluorescent labels and having a diameter smaller than the maximum diameter of the effector cell are the living effector cells, and the objects carrying the dead cell fluorescent label and having a diameter smaller than the maximum diameter of the effector cell are the dead effector cells.

In some embodiments, operation 210 further includes:

operation 211, obtaining the bright-field microscopic images of the fixed areas of the co-culture sample;

operation 212, determining the image-identifiable features that characterize the cell properties of the plurality of objects in the co-culture sample;

operation 213, obtaining at least one fluorescence microscopic image of the fixed areas of the co-culture sample, and the imaging parameters of the at least one fluorescence microscopic image are determined based on the image-identifiable features of the plurality of objects.

The bright-field microscopic image is an image acquired by the image acquisition device 140 irradiating the cell sample with a bright-field light source. The background of the field of view in bright-field microscopic images is bright, while the edges of cells in the cell sample are dark.

The fluorescence microscopic image is an image acquired after the image acquisition device 140 irradiates the cell sample with an excitation light source to cause the cell sample to emit fluorescence. The fluorescence microscopic images reflect the shape and location of cells in cell samples.

In some embodiments, the formats of the microscopic images may include the Joint Photographic Experts Group (JPEG) image format, the Tagged Image File Format (TIFF) image format, the Graphics Interchange Format (GIF) image format, the Kodak Flash PiX (FPX) image format and Digital Imaging and Communications in Medicine (DICOM) image format, or the like.

In some embodiments, the imaging parameters of at least one fluorescence microscopic image include fluorescence channel types and excitation light wavelengths. The fluorescence channel types and the corresponding excitation light wavelengths of the fluorescence microscopic images used by the detection system 100 for image analysis are determined according to the image-identifiable features of the cell properties of the plurality of objects in the co-culture sample.

In the case where the co-culture sample is obtained by labeling the cells with three fluorescent labels, the imaging parameters of at least one fluorescence microscopic image are determined from specific image-identifiable features of the cell properties of the plurality of objects in the co-culture sample. In some embodiments, it is determined that the image-identifiable features characterizing the cell properties of the objects are a combination of a preset fluorescent label, a total cell fluorescent label, and a dead cell fluorescent label, and the at least one fluorescence microscopic image includes a first fluorescence microscopic image, a second fluorescence microscopic image, and a third fluorescence microscopic image. The fluorescence channels for collecting the first fluorescence microscopic image and the excitation light wavelengths of the fluorescence channels match the preset fluorescent label, and the fluorescence channels for collecting the second fluorescence microscopic image and the excitation light wavelengths of the fluorescence channels match the total cell fluorescent label, the fluorescence channels for collecting the third fluorescence microscopic image and the excitation light wavelengths of the fluorescence channels match the dead cell fluorescent label.

In the case where the co-culture sample is obtained by labeling the cells with two fluorescent labels, the imaging parameters of at least one fluorescence microscopic image are determined from specific image-identifiable features of the cell properties of the plurality of objects in the co-culture sample. In some embodiments, it is determined that the image-identifiable features characterizing the cell properties of the objects are a combination of the preset fluorescent label and the dead cell fluorescent label, and the at least one fluorescence microscopic image includes the first fluorescence microscopic image and the third fluorescence microscopic image. The fluorescence channels for collecting the first fluorescence microscopic image and the excitation light wavelengths of the fluorescence channels match the preset fluorescent label, and the fluorescence channels for collecting the third fluorescence microscopic image and the excitation light wavelengths of the fluorescence channels match the dead cell fluorescent label.

In the case where the co-culture sample is obtained by labeling the cells with one fluorescent label, the imaging parameters of at least one fluorescence microscopic image are determined from specific image-identifiable features of the cell properties of the plurality of objects in the co-culture sample. In some embodiments, it is determined that the image-identifiable features characterizing the cell properties of the objects are a combination of the dead cell fluorescent label and different types of cell diameters, and the at least one fluorescence microscopic image is the third fluorescence microscopic image. The fluorescence channels for collecting the third fluorescence microscopic image and the excitation light wavelengths of the fluorescence channels match the dead cell fluorescent label.

In order to obtain more cell parameters related to evaluating at least one of a cell-killing efficacy or an immune activity, in some embodiments, operation 210 further includes the operation of obtaining a plurality of microscopic images of the control group in the fixed area of effector cell samples of the control group. The effector cell sample of the control group is a cell sample obtained by culturing the effector cells alone, and the fixed area of the target cell sample of the control group contains a plurality of first control objects with the image-identifiable features. The image-identifiable features characterizing the cell properties of second control objects are consistent with the image-identifiable features characterizing the cell properties of the objects.

In order to obtain more cell parameters related to evaluating at least one of a cell-killing efficacy or an immune activity, in some embodiments, operation 210 further includes the operation of obtaining a plurality of microscopic images of the control group in the fixed area of the target cell sample of the control group. The target cell sample of the control group is a cell sample obtained by culturing the target cells alone, and the fixed area of the target cell sample of the control group contains a plurality of second control objects with the image-identifiable features. The image-identifiable features characterizing the cell properties of second control objects are consistent with the image-identifiable features characterizing the cell properties of the objects.

Operation 220 is an operation of performing the image analysis. In operation 220, an image overlapping synthesis analysis or an image fusion analysis may be performed for the plurality of microscopic images to obtain the cell properties of the plurality of objects and make statistics to cell parameters associated with the cell properties. In some embodiments, the image analysis module may perform operation 220.

In some embodiments, the image overlapping synthesis analysis may be performed for the plurality of microscopic images to obtain the cell properties of the plurality of objects and make statistics to cell parameters associated with the cell properties. For a specific description of performing the image overlapping synthesis analysis for the plurality of microscopic images, please refer to FIG. 3 and its related descriptions, which will not be repeated here.

In some embodiments, the image fusion analysis may be performed for the plurality of microscopic images to obtain the cell properties of the plurality of objects and make statistics to cell parameters associated with the cell properties. In some embodiments, the image fusion analysis may be performed for the plurality of microscopic images to obtain the cell properties of the plurality of objects, and the making statistics to the cell parameters associated with the cell properties further includes:

obtaining the fused image based on the plurality of microscopic images;

analyzing the fused image to obtain the cell properties of the plurality of objects, and make statistics to the cell parameters associated with the cell properties.

Figure 5:
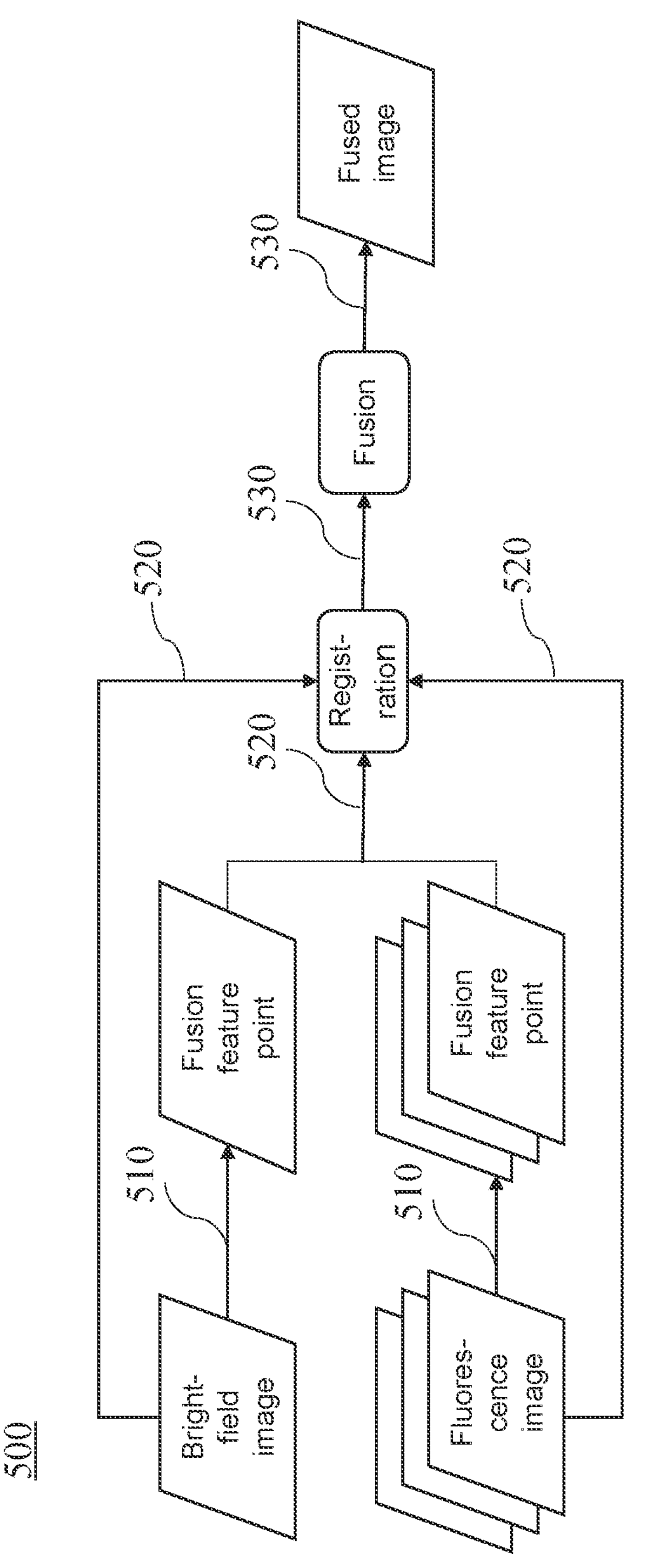
FIG. 5 is a flowchart illustrating an exemplary process for obtaining a fused image according to some embodiments of the present disclosure.

For a specific description of obtaining the fused image, reference may be made to FIG. 5 and related descriptions, which will not be repeated here. For a specific description of analyzing the fused image, reference may be made to FIG. 6 and related descriptions, which will not be repeated here.

Cell parameters are statistical data that may be used to evaluate at least one of the cell-killing efficacy or the immune activity. In some embodiments, the cell parameters may include first cell parameters related to the cell properties of the plurality of objects of the co-culture sample. The first cell parameters may be obtained by differential counting and making statistics to the plurality of objects based on the cell properties. In some embodiments, the first cell parameters may include one or more of a total count of the target cells and the effector cells, a total count of the target cells, a total count of the living target cells, a total count of the dead target cells, a death rate of the target cells, a total count of the effector cells, a total count of the living effector cells, a total count of the dead effector cells, and a death rate of the effector cells. Specifically, the death rate of the target cells and the death rate of the effector cells are calculated using the following equation:

the death rate of the target cells=total count of the dead target cells/total count of the target cells×100%;

the death rate of the effector cells=total count of the dead effector cells/total count of the effector cells×100%.

In order to obtain more cell parameters related to evaluating at least one of the cell-killing efficacy or the immune activity, in some embodiments, operation 220 further includes performing the image overlapping synthesis analysis based on the plurality of microscopic images of the control group in the target cell sample of the control group to obtain the cell properties of the plurality of first control objects, and make statistics to the cell parameters associated with the cell properties.

In some embodiments, the cell parameters may further include second cell parameters related to the cell properties of the plurality of first control objects of the target cell sample of the control group. The second cell parameters may be obtained by differential counting and making statistics to the plurality of first control objects based on the cell properties. In some embodiments, the second cell parameters may include one or more of a total count of target cells in the control group, a total count of the living target cells in the control group, a total count of the dead target cells in the control group, a death rate of the target cells in the control group, and a cell-specific killing rate. Specifically, the death rate of the target cells in the control group, and the cell-specific killing rate are calculated using the following equation:

The death rate of the target cells in the control group=total count of the dead target cells in the control group/total count of target cells in the control group×100%;

The cell-specific killing rate=the death rate of the target cells−the death rate of the target cells in the control group.

In order to obtain more cell parameters related to evaluating at least one of the cell-killing efficacy or the immune activity, in some embodiments, operation 220 further includes performing the image overlapping synthesis analysis based on the plurality of microscopic images of the control group in the effector cell samples of the control group to obtain the cell properties of the plurality of second control objects, and make statistics to the cell parameters associated with the cell properties.

In some embodiments, the cell parameters may further include third cell parameters related to the cell properties of the plurality of second control objects of the effector cell samples of the control group. The third cell parameters may be obtained by differential counting and make statistics to the plurality of second control objects based on the cell properties. In some embodiments, the third cell parameters may include one or more of a total count of effector cells in the control group, a total count of the living effector cells in the control group, a total count of the dead effector cells in the control group, a death rate of the effector cells in the control group, and a self-injury rate of the effector cells. Specifically, the death rate of the effector cells in the control group and the self-injury rate of the effector cells are calculated using the following equation:

The death rate of the effector cells in the control group=total count of the dead effector cells in the control group/total count of effector cells in the control group×100%;

the self-injury rate of the effector cells=the death rate of the effector cells−the death rate of the effector cells in the control group.

Operation 230 is an operation of evaluating at least one of the cell-killing efficacy or the immune activity. In operation 230, at least one of the cell-killing efficacy or immune activity of the effector cells is evaluated based on the cell parameters. In some embodiments, the evaluation module may perform operation 230.

In some embodiments, a combination of one or more of the death rates of the target cells, the death rate of the effector cells, the cell-specific killing rate, and the self-injury rate of the effector cells in the cell parameters may be used to characterize at least one of the cell-killing efficacy or the immunity activity of the effector cells. Specifically, one cell parameter or a combination of a plurality of cell parameters may intuitively reflect at least one of the cell-killing efficacy or immune activity level of the effector cells by comparing with a parameter threshold. For example, taking one cell parameter or a combination of the plurality of cell parameters of a selected control sample as the parameter threshold, and according to compare the corresponding cell parameters or combination of cell parameters of the test sample with the parameter threshold, at least one of the cell-killing efficacy or the immune activity of the effector cells of the test sample may be evaluated relative to the control sample. The control sample is selected according to the different evaluation purposes. As another example, using the selected interval estimate of the overall mean value of a cell parameter or a combination of a plurality of cell parameters in a control group comprising a plurality of control samples as the parameter threshold, and according to compare the corresponding cell parameters or combination of cell parameters of the test sample with the parameter threshold, at least one of the cell-killing efficacy or the immune activity of the effector cells of the test sample may be evaluated relative to the control sample. The control group is selected according to the different evaluation purposes.

In some embodiments, evaluating at least one of the cell-killing efficacy or immune activity of the effector cells based on the cell parameters may further include: comparing the death rate of the target cells with a death rate threshold, wherein the death rate threshold includes an upper limit and a lower limit, and evaluating at least one of the cell-killing efficacy or the immune activity of the effector cells according to the comparison result.

For example, in the application scenario of drug screening, tumor cells (target cells) and natural killer cells (effector cells) of blank control group mice (regular gavage with distilled water) are co-cultured, and the above detection method or detection system is used to detect the death rate of the target cells in co-culture sample of the blank control group mice. Through the BootStrap method, based on the death rate data of the target cells of the blank control group mice, the average range of the death rate of the target cells was calculated as the death rate threshold, which was used to represent the overall average value of the death rate of the target cells in normal mice. Tumor cells and natural killer cells of experimental group mice (regular gavage with the drug to be tested) are co-cultured, and the above detection method or detection system is used to detect the death rate of the target cells in co-culture sample of the experimental group mice. Comparative analysis of the death rate of the target cells and the death rate threshold of the experimental group mice: if the death rate of the target cells of the experimental group mice is higher than the upper limit of the death rate threshold, at least one of the cell-killing efficacy or immune activity of the natural killer cell in the experimental group mice is higher than the normal level, indicating that the drug to be tested may improve at least one of the cell-killing efficacy or immune activity of the natural killer cells in mice; if the death rate of the target cells of the experimental group mice is between the upper and lower limits of the death rate threshold, at least one of the cell-killing efficacy or immune activity of the natural killer cell in the experimental group mice is at the normal level, indicating that the drug to be tested may not improve at least one of the cell-killing efficacy or immune activity of the natural killer cells in mice; if the death rate of the target cells of the experimental group mice is lower than the lower limit of the death rate threshold, at least one of the cell-killing efficacy or immune activity of the natural killer cell in the experimental group mice is lower than the normal level, indicating that the drug to be tested may reduce at least one of the cell-killing efficacy or immune activity of the natural killer cells in mice.

FIG. 3 is a flowchart illustrating an exemplary process for performing the image overlapping synthesis analysis on a plurality of microscopic images according to some embodiments of the present disclosure. In some embodiments, process 300 may be performed by the image analysis module. As shown in FIG. 3, the process 300 includes operations 310 to 340.

Operation 310 is an operation of extracting the contours of the objects in the plurality of microscopic images. In some embodiments, a plurality of object regions and corresponding contour information in each of the plurality of microscopic images are extracted.

The object region refers to the image region containing a single object in the microscopic image, and the edge of the object regions is the outer contour of the corresponding object.

The contour information may be related information that characterizes the contour features of the object. In some embodiments, the contour information may include one or more of object location information, object size information, and object fluorescence information. The object location information includes but is not limited to, the coordinate information of the outer contour pixel points of the object on the microscopic image, the coordinate information of the object contour feature points (such as center and centroid), or the like. The object size information includes but is not limited to diameter information and contour area information, or the like. The object fluorescence information includes but is not limited to fluorescent intensity information, color information, or the like.

For the specific description of extracting the contours of the objects in the microscopic image, please refer to FIG. 4 and the related descriptions, which will not be repeated here.

Operation 320 is an operation of performing the object overlapping determination for the plurality of microscopic images. In some embodiments, an object overlapping determination may be performed based on the plurality of object regions and the corresponding contour information in the plurality of microscopic images to obtain an overlapping determination result.

In some embodiments, the object overlapping determination comprises a primary overlapping determination based on a feature point coordinate distance calculation and a secondary overlapping determination based on an intersection ratio calculation. Further, operation 320 includes:

obtaining the overlapping determination result by, for each object region of the plurality of object regions in each microscopic image of the plurality of microscopic images, traversing each of the other object regions of the other microscopic images to perform the object overlapping determination;

wherein in the object overlapping determination process:

if two object regions that are being compared are determined to be overlapping in the primary overlapping determination, a determination result of the primary overlapping determination is designated as the overlapping determination result of the object overlapping determination in a present round; and if the two object regions that are being compared are determined not to be overlapping in the primary overlapping determination, performing the secondary overlapping determination based on the two object regions that are being compared, and a determination result of the secondary overlapping determination is designated as the overlapping determination result of the object overlapping determination in the present round.

In some embodiments, the object overlapping determination comprises a primary overlapping determination based on a feature point coordinate distance calculation and a secondary overlapping determination based on an intersection ratio calculation.

In some embodiments, the operation of the primary overlapping determination further includes:

determining the feature points and feature point coordinates of the two object regions based on the contour information corresponding to the two object regions to be determined, wherein the two object regions are located on different microscopic images respectively;

calculating the feature point coordinate distance of the two object regions;

comparing the feature points coordinate distance with a preset distance threshold, and determining whether the two object regions overlap, wherein when the feature point coordinate distance of the two object regions is less than or equal to the distance threshold, it is determined that the two object regions overlap. Otherwise, it is judged that they do not coincide.

The feature points are the feature pixel points of the object regions on the corresponding microscopic images. The feature point coordinates are the pixel coordinates of the feature points of the object regions on the corresponding microscopic image, which may be extracted based on the contour information of the object regions. In some embodiments, the feature point may be one of the centers of the object regions, the centroid of the object regions, and the center of gravity of the object regions. Preferably, the feature point may be the center of the object regions.

The distance threshold is the determination limit of coincidence or not in the primary overlapping determination. Ideally, if different microscopic images of the objects are collected in the same fixed area, the feature points coordinate distance of the corresponding regions of the object of the same object on different microscopic images may be zero. In practical situations, since the plurality of microscopic images include bright-field microscopic images and at least one fluorescence microscopic image, and is influenced by factors such as the wavelength of the light source (at least one of a bright-field light source or an excitation light source) used to collect each microscopic image, and the exposure time of the imaging channel (at least one of bright-field channel or fluorescence channel), etc. The corresponding regions of the object of the same object on different microscopic images may have a position offset of several pixels to more than a dozen pixels. Setting the distance threshold may provide a tolerance space for the primary overlapping determination based on the calculation of the feature point coordinate distance. In some embodiments, the distance threshold may be set based on at least one of the selected wavelengths of the light source of the image acquisition device or the selected imaging channel exposure time. In some alternative embodiments, the distance threshold may be set based on user input. The setting method of the distance threshold is not limited here.

In some embodiments, the operation of the secondary overlapping determination further includes:

- calculating the intersection ratio of the object regions based on the two object regions to be determined;
- comparing the intersection ratio of the object regions and a preset intersection ratio threshold, it is determined whether the two object regions overlap. When the intersection ratio of the object regions of the two object regions is greater than or equal to the intersection ratio threshold, it is determined that the two object regions overlap, otherwise, it is determined that they do not overlap.

The intersection ratio of the object regions is the ratio of the area of the intersection between the two object regions to the area of the union, which may be used to evaluate a degree of overlap between the two object regions.

The intersection ratio threshold is the judgment limit of coincidence or not in the secondary overlapping determination. In some embodiments, the intersection ratio may be set based on the user input.

Operation 330 is an operation of determining the cell properties of the objects.

In some embodiments, the cell properties of the objects may be determined merely based on the overlapping determination results. Specifically, the above manner for determining the cell properties of the objects is suitable for overlapping synthesis analysis of the plurality of microscopic images of co-culture samples carrying two fluorescent labels or three fluorescent labels.

Exemplarily, in the case where the co-culture sample is obtained by labeling the cells with three fluorescent labels, the three fluorescent labels are respectively the preset fluorescent label, the total cell fluorescent label, and the dead cell fluorescent label. A plurality of microscopic images required for the image overlapping synthesis analysis includes the bright-field microscopic images, the first fluorescence microscopic images matching the preset fluorescent label, the second fluorescence microscopic images matching the total cell fluorescent label, and the third fluorescence microscopic images matching the dead cell fluorescent label. The overlapping determination results of the object overlapping determination include a set of feature information displayed in the plurality of microscopic images of the fluorescent label features of each object, that is, the overlapping determination results include the set of fluorescent label feature information of each target. The overlapping determination results may be used to determine the cell properties of the objects. Based on the overlapping determination results, the operation of determining the cell properties of the objects further include:

- marking the objects with object regions overlapping on the bright-field microscopic image, the first fluorescence microscopic image and the second fluorescence microscopic image, and no object regions overlapping on the third fluorescence microscopic image, and determining the cell properties of the objects are the living target cells;
- marking the objects with object regions overlapping on the bright-field microscopic image, the first fluorescence microscopic image, the second fluorescence microscopic image, and the third fluorescence microscopic image, and determining the cell properties of the objects are the dead target cells;
- marking the objects with object regions overlapping on the bright-field microscopic image and the second fluorescence microscopic image, and no object regions overlapping on the first fluorescence microscopic image and the third fluorescence microscopic image, and determining the cell properties of the objects are the living effector cells;
- marking the objects with object regions overlapping on the bright-field microscopic image, the second fluorescence microscopic image, and the third fluorescence microscopic image, and no object regions overlapping on the first fluorescence microscopic image, and determining the cell properties of the objects are the dead effector cells;
- marking the objects that only exist in the object regions on the bright-field microscopic image, and no object regions overlapping on the first fluorescence microscopic image, the second fluorescence microscopic image, and the third fluorescence microscopic image, and determining the cell properties of the objects are cell debris or impurities.

Exemplarily, when the co-culture sample is obtained by labeling the cells with two fluorescent labels, the two fluorescent labels are the preset fluorescent label and the dead cell fluorescent label, respectively. The plurality of microscopic images required to perform the image overlapping synthesis analysis includes the bright-field microscopic image, the first fluorescence microscopic image matching the preset fluorescent label, and the third fluorescence microscopic image matching the dead cell fluorescent label. The overlapping determination results of the object overlapping determination include a set of feature information displayed in the plurality of microscopic images of the fluorescent label features of each object, that is, the overlapping determination results include the set of fluorescent label feature information of each target. The overlapping determination results may be used to determine the cell properties of the objects. Based on the overlapping determination results, the operation of determining the cell properties of the objects further include:

- marking the objects with object regions overlapping on the bright-field microscopic image and the first fluorescence microscopic image, and no object regions overlapping on the third fluorescence microscopic image, and determining the cell properties of the objects are the living target cells;
- marking the objects with object regions overlapping on the bright-field microscopic image, the first fluorescence microscopic image, and the third fluorescence microscopic image, and determining the cell properties of the objects are the dead target cells;
- marking the objects that only exist in the object regions on the bright-field microscopic image, and no object regions overlapping on the first fluorescence microscopic image and the third fluorescence microscopic image, and determining the cell properties of the objects are the living effector cells;

marking the objects with object regions overlapping on the bright-field microscopic image and the third fluorescence microscopic image, and no object regions overlapping on the first fluorescence microscopic image, and determining the cell properties of the objects are the dead effector cells.

In some embodiments, operation 330 includes:

extracting the diameter information of the objects in the overlapping determination result to determine the cell diameter, and obtain the diameter determination result;

determining the cell properties of the corresponding objects based on the overlapping determination result and the diameter determination result.

In some embodiments, the cell diameter determination further includes: comparing the diameter information of the objects with a preset minimum diameter of the target cells and a preset maximum diameter of the effector cells, and obtaining the diameter determination result; If the diameter of the object is greater than or equal to the minimum diameter of the target cell, the object is determined to be the target cell; If the diameter of the object is smaller than the minimum diameter of the effector cell, the object is determined to be the effector cell.

The performing the diameter determination based on the contour information of the object regions to obtain the diameter determination result further includes: comparing the diameter of the object regions with the preset minimum diameter of the target cells and the preset maximum diameter of the effector cells to determine the objects corresponding to the object regions as target cells or effector cells to obtain the diameter determination results.

Exemplarily, the co-culture sample is obtained by labeling the cells with one fluorescent label, and the fluorescent label is a dead cell fluorescent label. The plurality of microscopic images required to perform the image overlapping synthesis analysis includes the bright-field microscopic image and the third fluorescence microscopic image matching the dead cell fluorescent label. The overlapping determination results of the object overlapping determination include a set of feature information displayed in the plurality of microscopic images of the fluorescent label features and the cell diameter features of each object, that is, the overlapping determination results include the set of fluorescent label feature information and cell diameter feature information of each target. The overlapping determination results may be used to determine the cell properties of the objects. The operation of determining the cell properties of the objects further includes:

marking the objects with object regions overlapping on the bright-field microscopic image and the third fluorescence microscopic image, and the objects are determined as dead cells by the object overlapping determination; extracting the diameter information of the objects whose cell properties are the dead cells in the overlapping determination result; comparing the diameter information of the objects with the preset minimum diameter of the target cells and the preset maximum diameter of the effector cells, and further determining that the object whose diameter is greater than or equal to the minimum diameter of the target cell and whose cell property as the dead cell is the dead target cell, and further determining that the object whose diameter is smaller than the effector cell and the cell property as the dead cell is the dead effector cell;

marking the objects with object regions overlapping on the bright-field microscopic image, and no object regions overlapping on the third fluorescence microscopic image, and the objects are determined as living cells by the object overlapping determination; extracting the diameter information of the objects whose cell properties are the living cells in the overlapping determination result; Comparing the diameter information of the objects with the preset minimum diameter of the target cells and the preset maximum diameter of the effector cells, and further determining that the object whose diameter is greater than or equal to the minimum diameter of the target cell and whose cell property as the living cell is the living target cell, and further determining that the object whose diameter is smaller than the effector cell and the cell property as the living cell is the living effector cell.

Operation 340 is an operation of obtaining the cell parameters. In operation 340, the plurality of objects may be differentially counted and statistics may be made to the plurality of objects based on the cell properties to obtain the cell parameters. Specifically, according to the different cell properties determined in operation 330, all the objects may be differentially counted and statistics may be made to all the objects to obtain the cell parameters. For specific descriptions of the cell parameters, please refer to operation 220 and related descriptions, which will not be repeated here.

Process 300 may also include the operation of generating a superimposed image based on the plurality of microscopic images. In some embodiments, the image analysis module may perform image fusion for the plurality of microscopic images to generate the superimposed image. In some embodiments, the process 300 further includes the operation of marking the plurality of objects in the superimposed image based on the cell properties. For the specific description of the image fusion for the plurality of microscopic images, please refer to FIG. 5 and related descriptions, which will not be repeated here.

In some embodiments, the image analysis module may be connected to an output device (display screen) to output the generated unmarked superimposed image or the marked superimposed image. In some embodiments of the present disclosure, the object properties obtained by the image overlapping synthesis analysis are directly marked on the superimposed image and output to the user, so that the way to obtain the analysis result is faster, more intuitive, and more efficient.

FIG. 4 is a flowchart illustrating an exemplary process for extracting object regions of the microscopic images according to some embodiments of the present disclosure. In some embodiments, process 400 may be performed by the image analysis module. As shown in FIG. 4, the process 400 includes operations 410 to 430.

Operation 410 is an operation of denoising the microscopic images. In operation 410, a filtering processing may be performed based on each of the plurality of microscopic images to obtain a plurality of denoised microscopic images. In some embodiments, the filtering processing includes at least one of a median filtering or a Gaussian filtering.

Operation 420 is an operation of binarizing the microscopic image. In operation 420, a binarization processing may be performed based on each of the plurality of denoised microscopic images to obtain a plurality of binarized microscopic images. The binarization processing is the process of making the plurality of microscopic images appear in a black-and-white manner.

Operation 430 is an operation of image segmentation and contour extraction. In operation 430, a segmentation of the plurality of objects may be performed based on each of the plurality of binarized microscopic images to extract the plurality of object regions and the corresponding contour information. The segmentation of objects is the process of dividing the binarized microscopic image into several object regions containing a single object and extracting the information of the object of interest. In some embodiments, the segmentation of objects is one of threshold segmentation, region growing method, watershed segmentation, and statistical segmentation.

FIG. 5 is a flowchart illustrating an exemplary process for obtaining a fused image according to some embodiments of the present disclosure. In some embodiments, process 500 may be performed by the image analysis module. As shown in FIG. 5, the process 500 includes operations 510 to 530.

In operation 510, extracting at least one fusion feature point in each of the plurality of microscopic images.

The fusion feature points are the pixel points of the same spatial point(s) on the co-culture sample in the plurality of microscopic images (bright-field microscopic image and at least one fluorescence microscopic image).

In some embodiments, the fusion feature points may correspond to the same object feature on the co-culture sample. In some embodiments, the same object feature may include a color feature, a texture feature, a shape feature, or the like. For example, if the shape feature of an object in the co-culture sample is a certain arc on the object, the fusion feature point is the pixel point corresponding to the arc in the plurality of microscopic images. In some embodiments, the image analysis module may search for the fusion feature points by manual search, automatic search, and semi-automatic search. In some embodiments, the image fusion module may also select the found fusion feature points through similarity measurement. In some embodiments, the similarity measurement may include any combination of one or more of mutual information-based measures, Fourier analysis-based measures, or the like.

In some embodiments, the fusion feature points of the plurality microscopic images may also correspond to the same location coordinates on the co-culture sample. For example, when the bright-field microscopic image and the at least one fluorescence microscopic image are collected in a certain fixed area of the co-culture sample, the fusion feature point may be a central location point on the bright-field microscopic image and the at least one fluorescence microscopic image.

In operation 520, the plurality of microscopic images are registered based on the corresponding fusion feature points of the plurality of microscopic images.

Registration is the determination of the correspondence between the plurality of spatial points on the co-culture sample and the pixel points in the plurality of microscopic images. In some embodiments, the image analysis module may find the correspondence through a registration algorithm.

Exemplarily, the image analysis module may use the registration algorithm based on a correspondence between at least part of the pixel points on a certain arc on a certain object in the bright-field microscopic image and the arc on at least part of the pixel points on the certain arc on the cell in at least one fluorescence microscopic image, and find a correspondence between the bright-field microscopic image and the at least one fluorescence microscopic image.

In some embodiments, the registration algorithms may include point-based registration algorithms (e.g., signature-based registration algorithms), curve-based registration algorithms, surface-based registration algorithms (e.g., surface contour-based registration algorithms), spatial alignment registration algorithms, cross-correlation configuration registration algorithms, mutual information-based registration algorithms, sequential similarity detection algorithms (SSDA), nonlinear transformation registration algorithms, B-spline registration algorithms, or the like, or any combination thereof.

In operation 530, the fused image is obtained by fusing the plurality of registered microscopic images based on at least one of a transparency or a chroma.

Fusion is the synthesis of information from the plurality of microscopic images into one microscopic image. In order to make the fused image include the shape information of the object and the color information displayed by the object in the plurality of microscopic images (bright-field image and at least one fluorescence microscopic image) at the same time, the image analysis module may fuse the registered plurality of microscopic images.

In some embodiments, the image fusion module may fuse the registered plurality of microscopic images based on the transparency. The fusion based on the transparency is to overlap microscopic images with different transparency and the overlapped plurality of microscopic images as a fused image. In some embodiments, the fusion based on the transparency may include Alpha fusion.

In some embodiments, the image fusion module may perform fusion based on the chroma. The Fusion based on the chroma is to perform a specific operation on the chroma of different microscopic images to obtain the chroma of the fused image, thereby obtaining the fused image. For example, the pixel point A' in the registered bright-field microscopic image has a corresponding relationship with the pixel point A" in the fluorescence microscopic image, based on the average value of each color component of the chroma RGB (220, 200, 100) of the pixel point A' and the chroma RGB (0, 200, 200) of the pixel point A", may obtain the chroma RGB (110, 200, 150) of the corresponding pixel A in the fused image.

In some embodiments, the image analysis module may further fuse the fused image obtained based on the transparency and the fused image obtained based on the chroma to obtain a final fused image.

Some embodiments of the present disclosure fuse the bright-field microscopic images and the fluorescence microscopic images based on at least one of transparency or chroma, and may fuse the color features of objects in different fluorescence microscopic images while preserving the morphological features of the objects in the different images, so that the fused image contains more information, thereby improving at least one of the accuracy of the cell-killing efficacy or the immune activity.

In some embodiments, the fusion may also include, but is not limited to, a combination of one or more of a Poisson fusion algorithm, a linear fusion algorithm, and a Collage algorithm.

Figure 6:
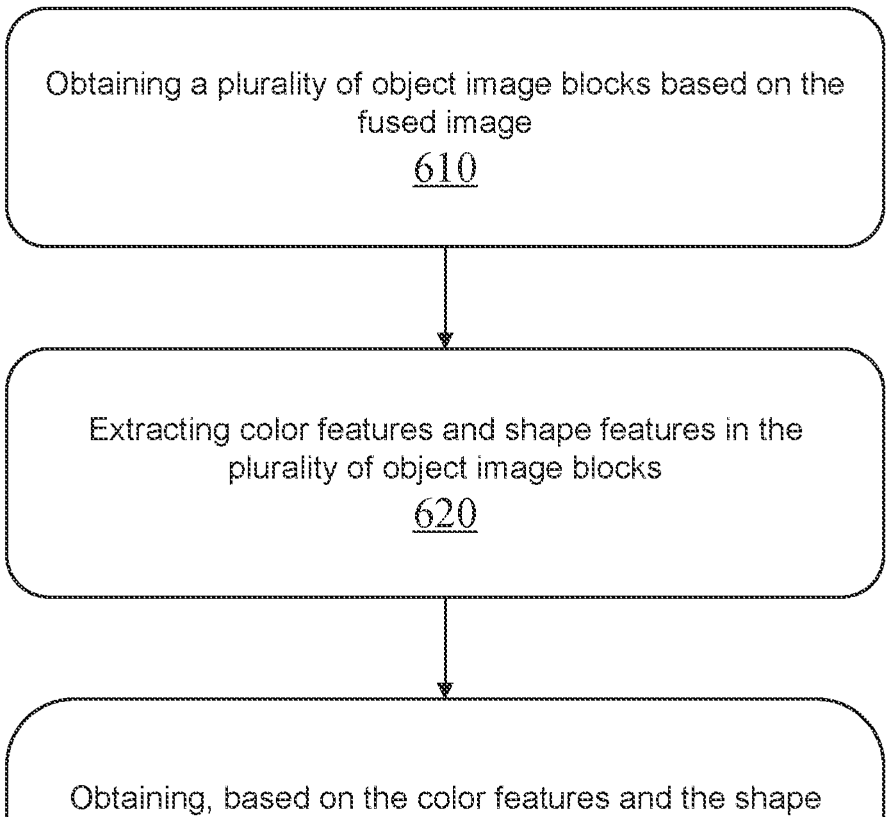
FIG. 6 is a flowchart illustrating an exemplary process for analyzing the fused image according to some embodiments of the present disclosure.

FIG. 6 is a flowchart illustrating an exemplary process for analyzing the fused image according to some embodiments of the present disclosure. In some embodiments, process 600 may be performed by the image analysis module. As shown in FIG. 6, the process 600 includes the following operations.

In operation 610, a plurality of object image blocks may be obtained based on the fused image.

The object image block is an image block containing a single object. In some embodiments, the image analysis module may obtain the object image blocks from the fused image through a detection algorithm.

In some embodiments, the detection algorithm may segment the fused image and detect a single object according to the features of the segmented image blocks. Specifically, the detection algorithm may first extract a plurality of image blocks from the fused image through a multi-scale sliding-window, selective search, neural network, or other methods, and then extract initial features of the plurality of image blocks, and finally determine whether the image block is the object image block based on the initial features of the image block. The initial features are the shallow features of the image block. For example, the initial features may only reflect whether the image block contains closed lines, but may not reflect the specific shape of the lines.

In operation 620, the color feature and shape feature of the object image blocks may be extracted.

The color feature is related to information characterizing the color of the object image block, and may reflect the color of the object in the object image block. In some embodiments, the color feature may be represented by the chroma of each pixel point in the object image block on different color components. For example, the color feature may be represented by the chroma of each pixel point in the object image block on red component R, green component G, and blue component B, respectively. In some embodiments, the color feature may be represented in other ways (e.g., color histograms, color moments, color sets, etc.). For example, histogram statistics are performed on the chroma of each pixel point in the color component of the object image block to generate a histogram representing color features. As another example, a specific operation (e.g., mean, squared difference, etc.) is performed on the chroma of each pixel point in the color component of the object image block, and the result of the specific operation represents the color features of the object image block.

In some embodiments, the image analysis module may extract the color features of the object image block through a color feature extraction algorithm. The color feature extraction algorithms include the color histograms, the color moments, the color sets, color aggregation vectors and color correlation graphs. For example, the image analysis module may count gradient histograms based on the chroma of each pixel point in each color component of the object image block, so as to obtain the color histograms. As another example, the image analysis module may divide the object image block into a plurality of regions, and use the set of binary indexes of the plurality of regions established by the chroma of each pixel point in each color component of the object image block to determine the color sets of the object image block.

The shape feature is related information that characterizes the contour and the object region image block and may reflect the shape of the object in the object image block.

In some embodiments, the image analysis module may obtain the shape features by using the boundary feature method, the Hough transformation detection parallel line method, the boundary direction histogram method, the Fourier shape descriptors, the shape factor, the Finite Element Method or FEM, the Turning method and the Wavelet Deor method, or the like.

In operation 630, the cell properties of the plurality of objects may be obtained based on the color features and the shape features of the plurality of object image blocks, and statistics may be made to the cell parameters associated with the cell properties.

In some embodiments, the image analysis module may determine the color and shape of the plurality of objects corresponding to the plurality of object image blocks in the fused image based on the color features and shape features of the plurality of object image blocks, and then obtain the cell properties of the object based on the color and shape of each object, and make statistics to the cell parameters associated with the cell properties.

Figure 7:
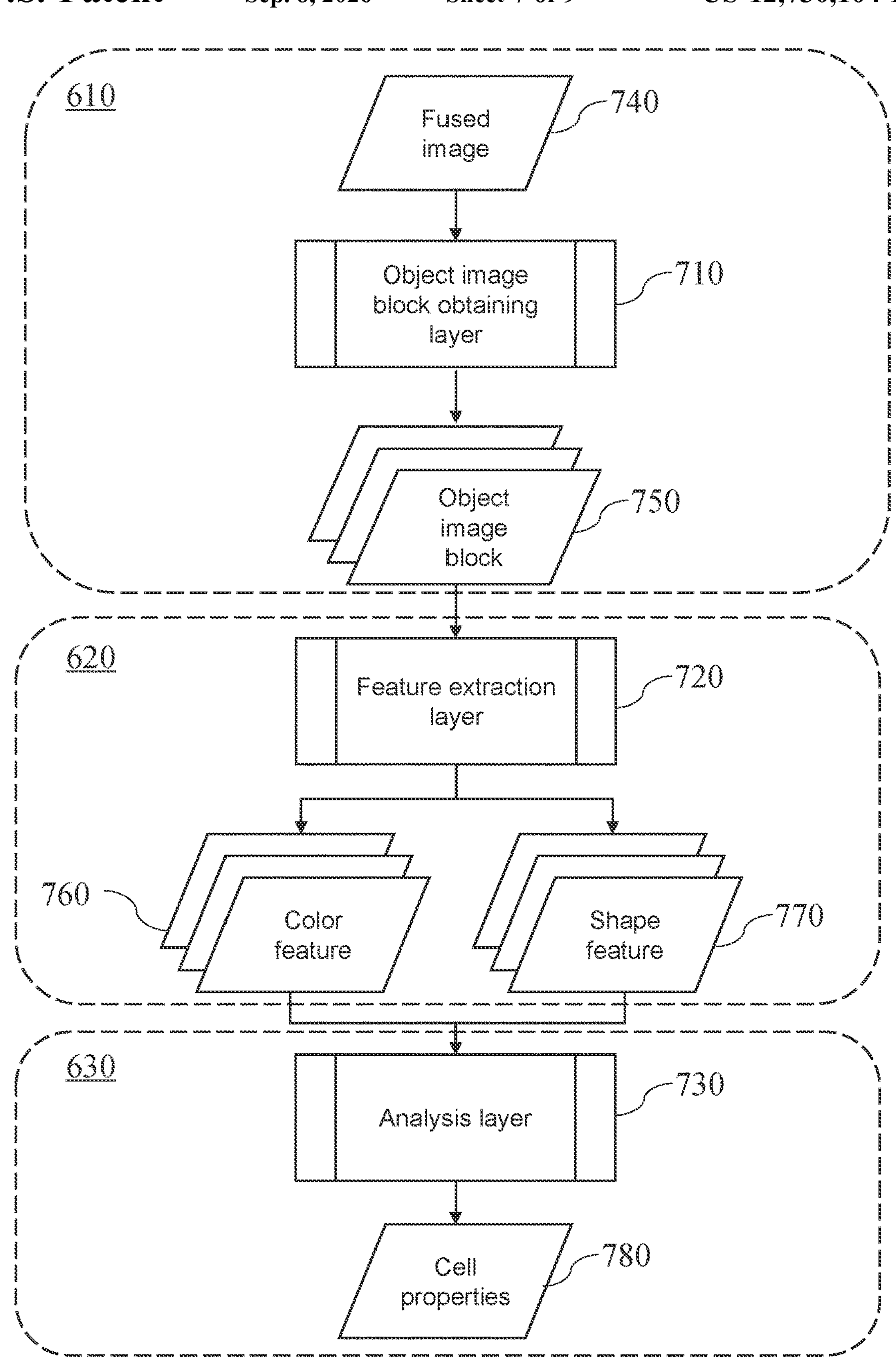
FIG. 7 is a schematic diagram illustrating an exemplary image recognition model according to some embodiments of the present disclosure.

For more related descriptions of obtaining the cell properties of the object, please refer to FIG. 7 and related descriptions, which will not be repeated here.

Some embodiments of the present disclosure determine the cell properties of each object in the fused image based on the color features and shape features of the object image blocks, and then make statistics to and analyze the cell parameters based on the corresponding cell properties of each object, which may improve the detection accuracy of at least one of the cell-killing efficacy or immune activity.

In some embodiments, the image analysis module may process the fused image based on the image recognition model to obtain the cell properties of the plurality of objects, and make statistics to the cell parameters associated with the cell properties. The image recognition model may be a machine-learning model with preset parameters. The machine-learning models that may be used as the image recognition models include, but are not limited to, object detection models, semantic segmentation models, instance segmentation models, or the like. The preset parameters refer to model parameters learned during a training process of the machine-learning model. Taking a neural network as an example, the model parameters include weight and bias.

FIG. 7 is a schematic diagram illustrating an exemplary image recognition model according to some embodiments of the present disclosure.

As shown in FIG. 7, the image recognition model may include an object image block obtaining layer 710, a feature extraction layer 720, and an analysis layer 730. For example, the image analysis module may implement operations 610-630 by using the image recognition model to obtain the cell properties of the plurality of objects, and make statistics to the cell parameters associated with the cell properties. Specifically, operation 610 may be implemented based on the object image block obtaining layer 710, operation 620 may be implemented based on the feature extraction layer 720, and operation 630 may be implemented based on the analysis layer 730.

In some embodiments, the input of the object image block obtaining layer 710 is the fused image 740 and the output is a plurality of object image blocks 750. In some embodiments, the type of the object image block obtaining layer may include, but is not limited to, a Visual Geometry Group Network model, an Inception NET model, a Fully Convolutional Network model, a segmentation network model, and a Mask-Region Convolutional Neural Network models, or the like.

In some embodiments, the input of the feature extraction layer 720 is the plurality of object image blocks 750, and the output is the color feature 760 and the shape feature 770 corresponding to each object image block. In some embodiments, the type of the feature extraction layer may include, but is not limited to, a Convolutional Neural Networks (CNN) model such as ResNet, ResNeXt, SE-Net, DenseNet, MobileNet, ShuffleNet, RegNet, EfficientNet, or Inception, or a Recurrent Neural Network Model.

In some embodiments, the input of the analysis layer 730 is the color feature 760 and the shape feature 770 corresponding to each object image block, and the output is the cell properties 780 of the plurality of objects and the counted cell parameters associated with the cell properties. In some embodiments, the type of the analysis layer may include, but is not limited to, a fully connected layer, a deep neural network (DNN), or the like.

In some embodiments, the preset parameters of the image recognition model are generated through the training process. For example, the model obtaining module may train an initial image recognition model in an end-to-end manner based on a plurality of training samples with labels to obtain the image recognition model. Training samples include sample fused images with labels. The labels of the training samples are the cell properties of the objects in the sample fused images and the cell parameters associated with the cell properties. In some embodiments, the labels of the training samples may be obtained by manual labeling.

In some embodiments, the image recognition model may be pre-trained by the processing device or a third party and stored in the storage device, and the processing device may directly call the image recognition model from the storage device.

Some embodiments of the present disclosure analyze the fused image based on the image recognition model, and obtain the cell properties of the object and the cell parameters associated with the cell properties, which may improve the detection efficiency of at least one of the cell-killing efficacy or immune activity; and an image recognition model may be obtained for obtaining different cell properties and cell parameters based on the different labels of the training samples, which may improve the applicability and pertinence of the detection of the at least one of the cell-killing efficacy or immune activity.

One of the embodiments of the present disclosure provides the application of a method or system for detecting at least one of the cell-killing efficacy or immune activity in the detection of the cell-killing efficacy, the immune activity of effector cells, the preparation of immune products, the quality control of immune products, or the evaluation of individual immune function.

Cell killing has become a crucial operation in the development and quality control process of antibody drugs. In the process of antibody drugs development and production, it is necessary to identify the biological functions of the obtained antibody drugs, including ADCC (antibody-dependent cytotoxicity) mediated by antibody drugs, CDC (complement-dependent cytotoxicity) and ADCP (Antibody-dependent cell-mediated phagocytosis) effect detection. The method or system for detecting at least one of the cell-killing efficacy or immune activity provided by some embodiments of the present disclosure may directly evaluate the biological activity of the above-mentioned antibody drugs by detecting the cell-killing efficacy. In addition, cell therapy drugs represented by CAR-T cell therapy also need to perform biological functional evaluation and quality control of the prepared CAR-T cell drugs by detecting the cell-killing efficacy, so as to ensure the effectiveness and security of CAR-T cell drugs. The above-mentioned applications of the method or system for detecting at least one of the cell-killing efficacy or immune activity provided by some embodiments of the present disclosure all have positive significance.

The experimental methods in the following embodiments are conventional methods unless otherwise specified. The test materials used in the following embodiments are purchased from conventional biochemical reagent companies unless otherwise specified.

Embodiment 1—Magnetic Beads Isolation of Human Natural Killer Cells 1.1. 50 ml of human peripheral anticoagulant was taken and human PBMC was separated by Ficoll-Hypaque density gradient centrifugation.

1.2. The cells were centrifuged with 15 mL PBS (containing 2 mmol/L EDTA) at 300 g for 5 min, washed twice, and then suspended in PBS (containing 1% serum, 2 mmol/L EDTA) to $1\times10^8$ cells/mL, and placed in 1.5 mL centrifugal tube at 4° C. for later use.

1.3. Anti-CD16 antibody was added to the cells (final concentration is 10 μg/mL), and the cells were incubated at 4° C. for 30 min.

1.4. The cells were washed twice with cold PBS (containing 2 mmol/L EDTA) at 700 g for 30 s; $1\times10^8$ cells were resuspended in 0.8 mL PBS (containing 1% serum, 2 mmol/L EDTA); 0.2 mL goat anti-mouse IgG-coated magnetic beads were added; and the cells were incubated at 4° C. for 30 min with shaking every 5 min.

1.5. The cells were washed twice with PBS (containing 2 mmol/L EDTA) at 700 g for 30 s, resuspended with 1 mL of PBS (containing 1% serum, 2 mmol/L EDTA), and reserved at room temperature for later use.

1.6. The MS column was installed on the magnet stand, pre-washed 3 times with 1 mL of PBS (containing 1% serum, 2 mmol/L EDTA); then the above cell suspension was added to the column; the effluent was collected, and then the effluent was added to the column; the column was washed 10 times with 1 mL of PBS (containing 2 mmol/L EDTA).

1.7. The separation column was removed from the magnetic field; the cells bound to the magnetic beads were washed with 3 mL PBS (containing 1% serum, 2 mmol/L EDTA), repeated 3 times; the cells were centrifuged at 300 g for 5 min, and resuspended in an appropriate amount of a culture medium; the cells were counted and reserved at 4° C. for later use.

Embodiment 2—Detection of Immune Activity of Natural Killer Cells 2.1. Target cell label Tumor cells (K562 cell line) were added into a suspension with a cell concentration of 1×105 cells/mL; 1 μL of CFSE with a concentration of 20 μM was added to 1 mL of the suspension for labeling, and the resultant suspension was incubated at 37° C. for 30 min in the dark;

after the incubation, the suspension was centrifuged at 400 g for 3 min at room temperature; the supernatant was removed, and 1 mL of serum-containing medium was added to obtain CFSE-labeled K562 cells.

2.2. Preparation of Natural Killer Cell suspension

An appropriate amount of natural killer cells prepared in Embodiment 1 was used, the cell concentration of which was adjusted to $1\times10^6$ cells/mL, and the natural killer cells were incubated at 4° C. for later use.

2.3. Cell co-culture

Experimental group: 100 μL of the CFSE-labeled K562 cells in operation 2.1 and 100 μL of natural killer cells in operation 2.2 were added to the sample holes of the 96-hole plate at the same time to obtain the experimental group; the effect-target ratio was set to 10:1; the cells were co-cultured for 4 hours in a 37° C. 5% $CO_2$ incubator. After the co-culture, Hoechst33342 (purchased from Thermofisher, USA) and PI dye (purchased from Sigma, USA) were added for staining to obtain the co-culture samples.

Control group: only 100 μL of the CFSE-labeled K562 cells in operation 2.1 and 100 μL of culture medium were added to the sample holes of the 96-hole plate to obtain the target cells of the control group. Only 100 μL of natural killer cells from operation 2.2 and 100 μL of culture medium were added to the sample holes of the 96-hole plate to obtain natural killer cells of the control group. Referring to the method of the experimental group to culture and stain the target cells of the control group and the natural killer cells of the control group, a target cell sample of the control group and a natural killer cell sample of the control group were obtained.

2.4. Microscopic imaging

The co-culture sample obtained in operation 2.3, the target cell sample of the control group, and the natural killer cell sample of the control group were added to the hemocytometer respectively.

Experimental group: the hemocytometer with the co-culture sample was placed on the sample stage of the detection instrument, and microscopic imaging was performed in the fixed area of the co-culture sample with bright-field and microfluorescence channels matching three fluorescent labels, respectively, thereby obtaining the bright-field microscopic images and three fluorescence microscopic images.

The information and order of the three fluorescence channels are as follows:

FL1: Ex 375 nm, Em 460 nm; FL2: Ex 480 nm, Em 535 nm; FL3: Ex 525 nm, Em 600LP;

the FL1 channel excited and collected Hoechst33342 fluorescence light, the FL2 channel excited and collected CFSE fluorescence light, the FL3 channel excited and collected PI fluorescence light.

Control group: for the hemocytometer with the target cell sample of the control group and the natural killer cell sample of the control group, respectively, the bright-field microscopic images and fluorescence microscopic images of the control group were obtained by performing a microscopic imaging operation respectively according to the method of the experimental group.

2.5. Image overlapping synthesis analysis

Experimental group: the system for detecting at least one of the cell-killing efficacy or immune activity performs the image overlapping synthesis analysis, fluorescence microscopic images and bright-field microscopic images of the co-culture samples under the FL1 channel, FL2 channel, and FL3 channel. After the image overlapping operation, the detection system marks the same position where the cells are located. If there is only an FL1 signal at this position, then the number is marked and counted as a; if there are FL1 and FL2 signals at the same time here, then the number is marked and counted as b; if there are FL1 and FL3 signals at the same time here, the number is marked and counted as c; if there are FL1, FL2 and FL3 signals at the same time, the number is marked and counted as d.

Additionally, equations are customed and edited as follows:

total count of living target cells=$b$; total count of dead target cells=$d$;

the death rate of the target cells (%)=$d/(b+d)\times 100$;

total count of living natural killer cells=$a$; Total count of dead natural killer cells=$c$; and the death rate of natural killer cells (%)=$c/(a+c)\times 100$.

Figure 8:
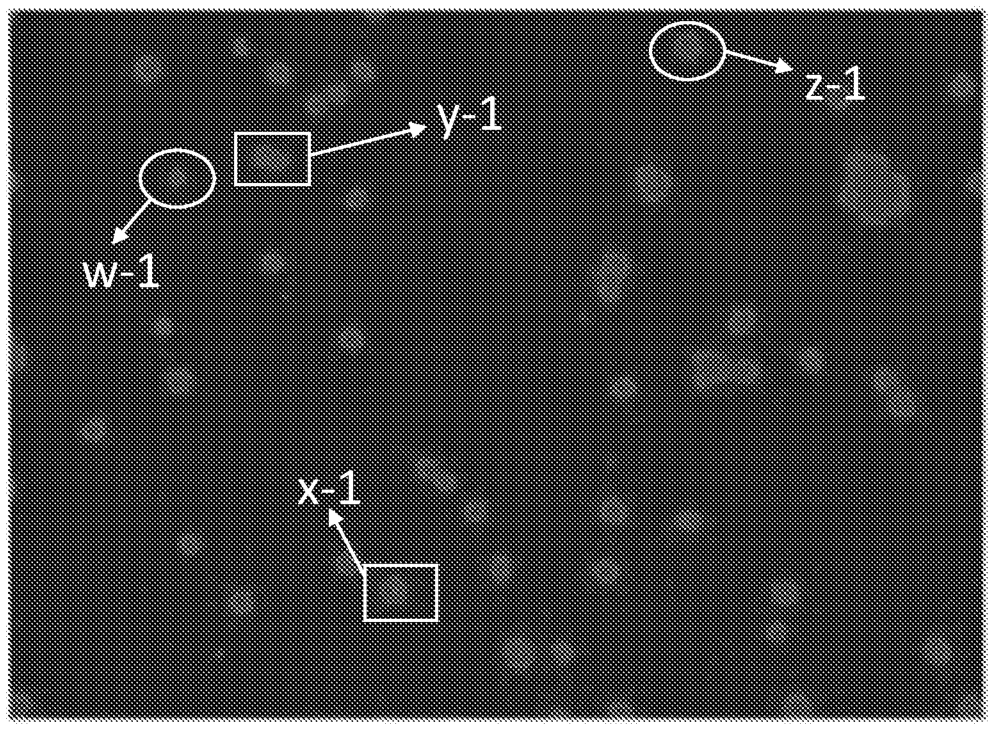
FIG. 8 is a fluorescence microscopic image collected by the FL1 channel in the first embodiment of the present disclosure.
Figure 9:
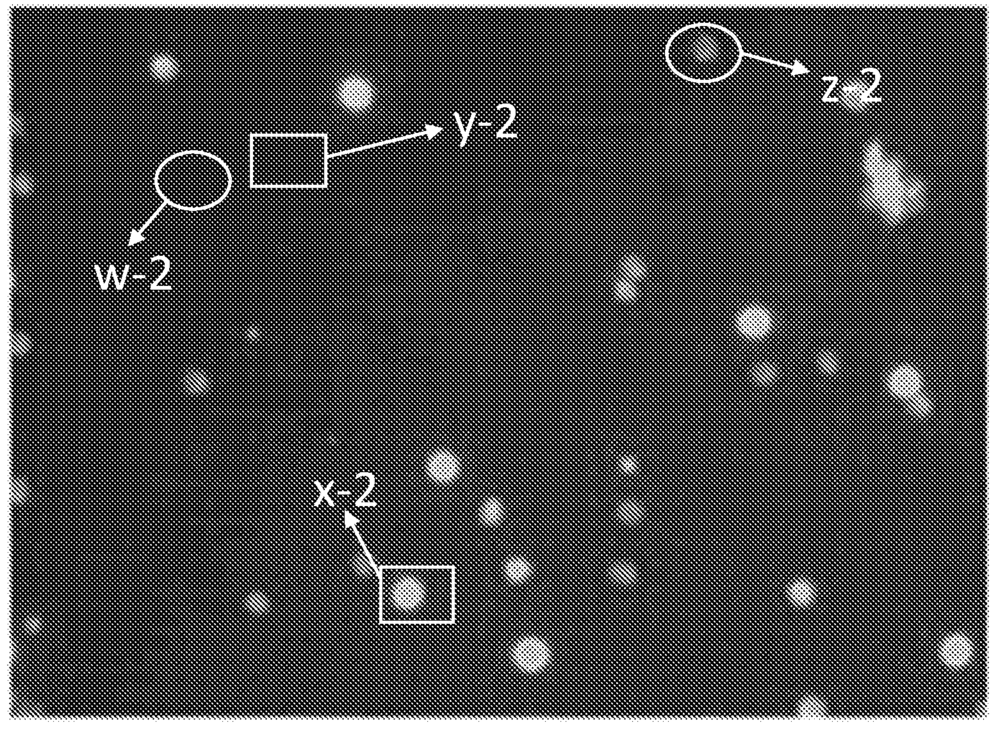
FIG. 9 is a fluorescence microscopic image collected by the FL2 channel in the first embodiment of the present disclosure.
Figure 10:
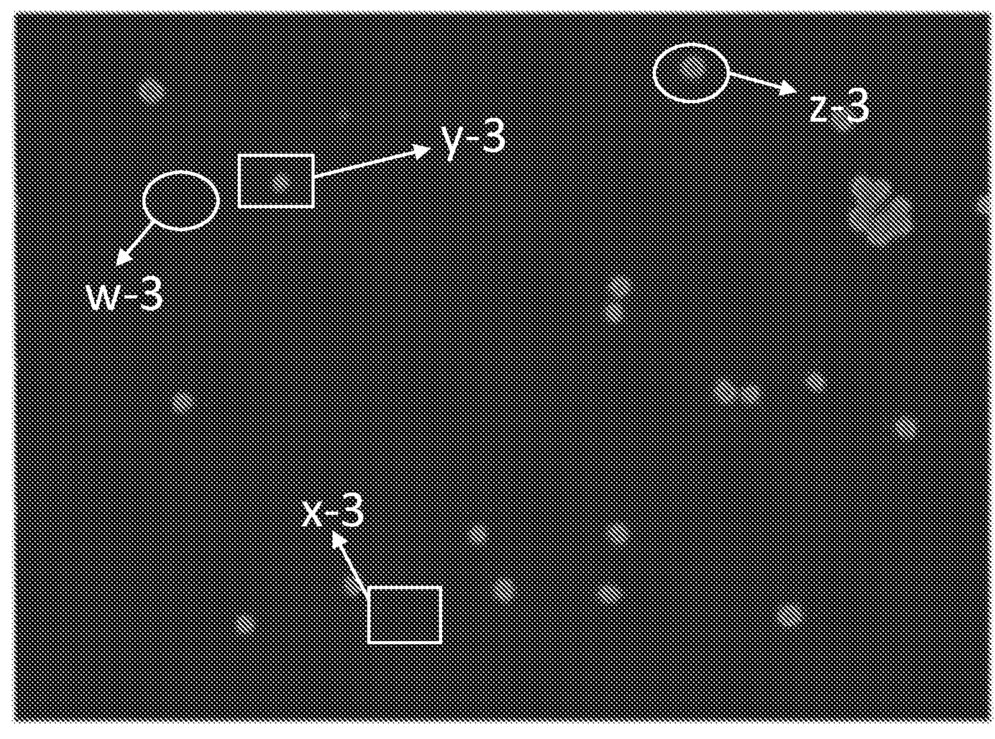
FIG. 10 is a fluorescence microscopic image collected by the FL3 channel in the first embodiment of the present disclosure.
Figure 11:
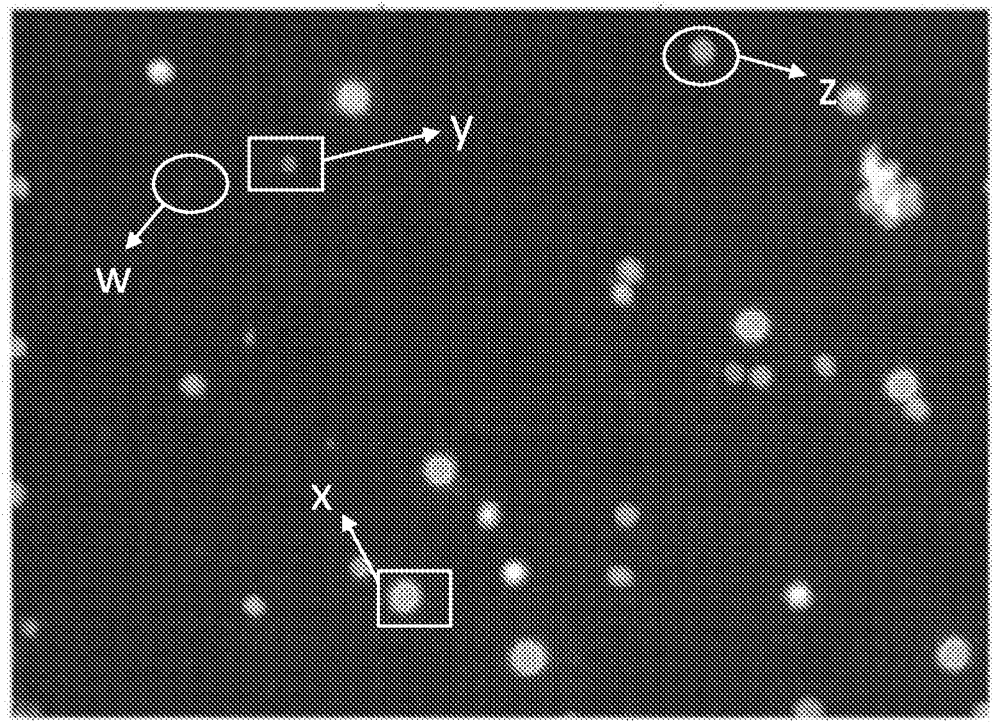
FIG. 11 is a superimposed image of the fluorescence microscopic images collected by the FL1, FL2, and FL3 channels in the first embodiment of the present disclosure.

FIG. 8 to FIG. 10 are fluorescence microscopic images collected by the FL1 channel, the FL2 channel, and the FL3 channel, respectively; FIG. 11 is a superimposed image of the fluorescence microscopic images collected by the FL1, FL2, and FL3 channels. The region w, region x, region y, and region z in FIG. 11 all contain objects. For the object in the region w, it has an FL1 signal at the overlapping regions w-1, w-2, and w-3 in FIG. 8 to FIG. 10, but has no FL2 signal and FL3 signal, and its cell properties are living natural killer cells. For the object in the region x, it has an FL1 signal and FL2 signal at the overlapping regions x-1, x-2, and x-3 of FIG. 8 to FIG. 10, respectively, but has no FL3 signal, and its cell properties are living target cells. For the object in the region y, it has an FL1 signal and FL3 signal at the overlapping regions y1, y2, and y3 of FIG. 8 to FIG. 10, respectively, but has no FL2 signal, and its cell properties are dead natural killer cells. For the object in the region z, it has an FL1 signal, FL2 signal, and FL3 signal at the overlapping regions z1, z2, and z3 in FIG. 8 to FIG. 10, and its cell properties are dead target cells.

After the analysis of the detection system, in FIG. 8 to FIG. 10, the total count of living natural killer cells is 9, the total count of living target cells is 15, the total count of dead natural killer cells is 2, and the total count of dead target cells is 28. Further, the death rate of the target cells is 65.11%, and the death rate of natural killer cells is 18.18%.

Control group: referring to the detection method of the experimental group, the image overlapping synthesis analysis was performed for the bright-field microscopic images and fluorescence microscopic images of the control group to obtain the death rate of the target cells in the control group and the death rate of the natural killer cells in the control group, so as to calculate the cell-specific killing rate and a self-injury rate of the natural killer cells.

The cell-specific killing rate (%)=the death rate of the target cells−the death rate of the target cells in the control group;

The self-injury rate of the natural killer cells (%)=the death rate of the effector cells−the death rate of the natural killer cells in the control group.

In the case of setting the control group, the influence of natural cell death and other conditions on the evaluation results of natural killer cell immune activity is excluded, and the detection accuracy is improved.

Embodiment 3—Detection of Immune Activity of Natural Killer Cells 3.1 Preparation of Natural Killer Cell suspension An appropriate amount of natural killer cells prepared in Embodiment 1 was used; the cell concentration was adjusted to $1\times10^6$ cells/mL; and the natural killer cells were added at 4° C. for later use.

3.2 Tumor cell label

Tumor cells (K562 cell line) were collected and added into a suspension with a cell concentration of $1\times10^5$ cells/mL; 1 μL of CFSE with a concentration of 20 μM was added to 1 mL of the suspension for labeling; and the suspension was incubated at 37° C. for 30 min in the dark;

after the incubation, the cell culture was centrifuged at 400 g for 3 min at room temperature; the supernatant was removed, and 1 mL of serum-containing medium was added to obtain CFSE-labeled K562 cells.

3.3. Cell co-culture

Experimental group: 100 μL of the natural killer cell suspension in operation 3.1 and 100 μL of CFSE-labeled K562 cells in operation 3.2 were added to the sample holes of a 96-hole plate; the effect-target ratio was set to 10:1; the cells were co-cultured for 4 hours in a 37° C. 5% $CO_2$ incubator. After the co-culture, 2 μL of a dead cell dye PI was added to the cells and the cells were incubated at room temperature for 10 min to obtain co-culture samples.

Control group: only 100 μL of the CFSE-labeled K562 cells in operation 3.2 and 100 μL of a culture medium were added to the sample holes of a 96-hole plate to obtain target cells of the control group. Only 100 μL of natural killer cells from operation 3.1 and 100 μL of a culture medium were added to the sample holes of the 96-hole plate to obtain natural killer cells of the control group. The target cell sample of the control group and natural killer cell sample of the control group were obtained by culturing and staining the target cells of the control group and the natural killer cells of the control group according to the method of the experimental group.

3.4 Microscopic imaging

Experimental group: 20 μL of co-culture sample was added to the hemocytometer; the hemocytometer was placed on the sample stage of the detection instrument; microscopic imaging was performed for the fixed area of the co-culture sample with the bright-field channel, FL1 channel (matching a fluorescent dye CFSE), and FL2 channel (matching a fluorescent dye PI), respectively, to obtain the bright-field microscopic images and two fluorescence microscopic images.

The information and order of the two fluorescence channels are as follows:

FL1: Ex 480 nm, Em 535 nm; FL2: Ex 525 nm, Em 600LP.

The FL1 channel excited and collected CFSE fluorescence light, and the FL2 channel excited and collected PI fluorescence light.

Control group: for the hemocytometer with 20 μL of the target cell sample of the control group and 20 μL of the natural killer cell samples of the control group, respectively, the bright-field microscopic images and fluorescence microscopic images of the control group were obtained by performing microscopic imaging respectively according to the method of the experimental group.

3.5 Image synthesis analysis

Experimental group: the system for detecting at least one of the cell-killing efficacy or immune activity performs the image overlapping synthesis analysis for the fluorescence microscopic images under the bright field, the FL1 channel, and the FL2 channel. The objects of image recognition under the bright-field channel are total cells (including target cells and natural killer cells); the objects of image recognition under the FL1 channel are target cells (including living target cells and dead target cells); the objects of image recognition under the FL2 channel are total dead cells (including dead target cells and dead natural killer cells).

After the three images are overlapped, the detecting system marks the same position where the cells are located.

If there is no fluorescent signal, mark and count the number as a; If there is only an FL1 signal, the number is counted and marked as b; if there are FL1 and FL2 signals at the same time, the number is marked and counted as d; if there is only an FL2 signal, the number is counted and marked as c.

Refer to operation 2.5 of Embodiment 2 for the custom editing equation.

Control group: referring to the detection method of the experimental group, perform image overlapping synthesis analysis on the bright-field microscopic images and fluorescence microscopic images of the control group to obtain the death rate of the target cells in the control group and the death rate of the natural killer cells in the control group, so as to calculate the cell-specific killing rate and a self-injury rate of the natural killer cells. The equation refers to operation 2.5 of Embodiment 2.

3.6 Evaluation of immune activity

Comparing the death rate of the target cells with the death rate threshold. The death rate threshold is set according to different situations. In this embodiment, the upper limit of the death rate threshold is set to 40%, and the lower limit is set to 20%.

It should be noted that the upper and lower limits of the death rate threshold here need to be comprehensively assessed according to the actual situation, and the values here are only used as examples or references.

In the results of the detection results: in the experimental group with the death rate of the target cells greater than or equal to 40%, the immune activity of the natural killer cells is better; in the experimental group with the death rate of the target cells less than or equal to 20%, the immune activity of the natural killer cells is poor; In the experimental group with the death rate of the target cells is more than 20% and less than 40%, the immune activity of the natural killer cells is normal.

Embodiment 4—Detection of the Immune Activity of Natural Killer Cells 4.1. Preparation of Natural Killer Cell suspension An appropriate amount of natural killer cells were used and the cell concentration was adjusted to $1\times10^6$ cells/mL; the cells were placed at 4° C. for later use. The maximum diameter of the natural killer cells is 9 μm.

4.2. Preparation of tumor cells collect tumor cells (K562 cell line) and prepare them into a suspension with a cell concentration of $1\times10^5$ cells/mL, and then add 100 μL of K562 cells to the 96-hole plate. The minimum diameter of the K562 cells is 9 μm.

4.3. Co-culture of natural killer cells and tumor cells

Experimental group: Take 100 μL of the natural killer cell suspension in operation 4.1, and add it to the 96-hole plate with K562 cells, the effect-target ratio was set to 10:1, co-culture for 4 hours in a 37° C. 5% $CO_2$ incubator.

Control group: add only 100 μL of culture medium to 100 μL of target cells (as the target cell of the control group), and add only 100 μL of culture medium to 100 μL of natural killer cells (as the natural killer cell of the control group), and culture under the same conditions as the experimental group. At the time of detection, also use the same detection and analysis methods as the experimental group.

4.4. After 4 hours of co-culture, remove the supernatant, wash with PBS buffer, add 0.25% trypsin to digest the adherent cells, centrifuge, and resuspend in PBS to prepare a cell suspension.

4.5. After mixing the cell suspension in operation 4.4 with the 0.2% trypan blue solution at a volume ratio of 1:1, pipette 20 μL into a counting plate and place the counting plate on the sample stage of the detection instrument (the instrument used in this embodiment is the Countstar automatic cell counter).

4.6. After setting the trypan blue bright field detection program on the detection instrument, perform the detection.

4.7. The system detecting at least one of the cell-killing efficacy or immune activity performs image overlapping synthesis analysis on the image, and then counts the dead and living cells of different diameters in the image:

The specific correspondence is:

I. The information obtained in the experimental group is as follows:

the unstained cells with a diameter greater than or equal to 9 μm are living target cells, and the count of the living target cells is counted as a;

the stained cells with a diameter greater than or equal to 9 μm are dead target cells, and the count of the dead target cells is counted as b;

the unstained cells with a diameter of less than 9 μm are living effector cells, and the count of the living effector cells is counted as c;

the stained cells with a diameter of less than 9 μm are dead effector cells, and the count of the dead effector cells is counted as d.

II. In the target cell of the control group, the stained cells with a diameter of less than 9 μm are dead target cells, and the count of the dead target cells is counted as N.

III. In the effector cell of the control group, the stained cells with a diameter of less than 9 μm are dead effector cells, and the count of the dead effector cells is counted as M.

Therefore, the death rate of the target cells may be calculated by the following equation:

The death rate of the target cells=number of dead target cells/(number of living target cells+number of dead target cells)=$(b+d-M)/(a+b+d-M)\times 100\%$;

alternatively, the death rate of the target cells=number of dead target cells/(number of living target cells+number of dead target cells)=$(b+N)/(a+b+N)\times 100\%$.

The death rate of the effector cells may be calculated by the following equation:

The death rate of the effector cells=number of dead effector cells/(number of living effector cells+number of dead effector cells)=$(d-N)/(c+d-N)\times 100\%$.

At the same time, the specific killing rate of the target cells and the self-injury rate of the effector cells may also be calculated:

The special killing rate of the target cells (%)=the death rate of the target cells in the experimental group−the death rate of the target cells in the control group;

The self-injury rate of the effector cells (%)=the death rate of the effector cells in the experimental group−the death rate of the effector cells in the control group.

The possible beneficial effects of the embodiments of the present disclosure include but are not limited to: (1) the detection methods of some embodiments of the present disclosure may perform an image overlapping synthesis analysis based on the microscopic images collected by triple staining, double staining, or single staining of the co-culture product of target cells and effector cells, respectively, and the detection methods of some embodiments of the present disclosure may accurately and efficiently distinguish living target cells, dead target cells, living effector cells and dead effector cells, and additionally, the cell-killing rate and other cell parameters used to evaluate at least one of the cell-killing efficacy or immune activity may be calculated according to the actual detection requirements based on the count of cells with corresponding properties; (2) the detection methods of some embodiments of the present disclosure may simultaneously obtain the direct-reading image information and data processing results of the cell samples to be tested, and compared with the detection results provided by common detection methods such as flow cytometry, the obtained results are more intuitive, and cluster analysis and high-content analysis may be realized simultaneously on one instrument, and a plurality of data such as the cell death rate, the cell self-injury rate, and the cell-specific killing rate may be obtained, which reduces the detection operations and improves the detection efficiency, and the detection method is simple and the scope of application is wide; (3) the detection methods of some embodiments of the present disclosure may perform image overlapping synthesis analysis based on the microscopic images collected by using triple staining, double staining, or single staining of the co-culture product of target cells and effector cells respectively. Based on the shape feature and color feature of the object in the object image blocks contained in the fused image, the cell properties of the object and the cell parameters associated with the cell properties may be quickly obtained, which reduces the procedures and improves the efficiency of detection and analysis; (4) the detection methods of some embodiments of the present disclosure may detect the image-identifiable features of the co-culture sample in various combinations, and the scope of detection is wide.

It should be noted that different embodiments may have different beneficial effects. In different embodiments, the possible beneficial effects may be any one or a combination of the above, or any other beneficial effects that may be obtained. Those skilled in the art should understand that the above embodiments are only to illustrate the present disclosure, but not to limit the present disclosure. Any modification, equivalent replacement, and change in the spirit and principles of the present disclosure shall be included in the protection scope of the present disclosure.

What is claimed is:

1. A method for detecting at least one of a cell-killing efficacy or an immune activity, comprising:

obtaining a plurality of microscopic images of a fixed area of a co-culture sample with an image acquisition device, wherein the image acquisition device includes at least one of a metallographic microscope, a bright-field microscope, or a fluorescence microscope, the co-culture sample is a cell sample obtained by co-culturing target cells and effector cells, the fixed area of the co-culture sample includes a plurality of objects, wherein the plurality of objects are a cell group including cells with different properties, each of the plurality of objects having an image-identifiable feature, and a cell property of each of the plurality of objects being characterized by a collection of feature information of the image-identifiable feature of the object displayed in the plurality of microscopic images, wherein the cell property includes a cell type and a cell survival status, and the plurality of objects are a cell group including living target cells, dead target cells, living effector cells, and dead effector cells;

performing an image overlapping synthesis analysis for the plurality of microscopic images to obtain the cell properties of the plurality of objects and make statistics to cell parameters associated with the cell properties;

evaluating at least one of the cell-killing efficacy or the immune activity of the effector cells based on the cell parameters; and preparing immune products based on the cell-killing efficacy or the immune activity of the effector cells, wherein the performing an image overlapping synthesis analysis for the plurality of microscopic images to obtain the cell properties of the plurality of objects and make statistics to cell parameters associated with the cell properties comprises:

extracting, in each of the plurality of microscopic images, a plurality of object regions and corresponding contour information;

performing, for the plurality of microscopic images, an object overlapping determination based on the plurality of object regions and the corresponding contour information to obtain an overlapping determination result, wherein the overlapping determination result includes the collection of the feature information of the image-identifiable features of each of the plurality of objects displayed in the plurality of microscopic images, and the object overlapping determination includes a primary overlapping determination based on a coordinate distance calculation of feature points and a secondary overlapping determination based on a calculation of an intersection-union ratio;

determining the cell properties corresponding to the plurality of objects based on the overlapping determination result; and differentially counting and conducting statistical analysis of the plurality of objects based on the cell properties to obtain the cell parameters.

2. The method of claim 1, wherein among the plurality of objects, objects with different cell properties have different image-identifiable features, and the image-identifiable features include fluorescent label features.

3. The method of claim 2, wherein the co-culture sample is obtained by operations including:

obtaining a co-culture product by co-culturing the target cells carrying preset fluorescent labels and the effector cells carrying no fluorescent labels;

marking the co-culture product with total cell fluorescent labels and dead cell fluorescent labels after co-culturing the target cells and the effector cells for a predetermined time to obtain the co-culture sample, wherein among the plurality of objects in the fixed area of the co-culture sample, an object carrying a preset fluorescent label and a total cell fluorescent label is a living target cell, an object carrying a preset fluorescent label, a total cell fluorescent label, and a dead cell fluorescent label is a dead target cell, an object only carrying a total cell fluorescent label is a living effector cell, and an object carrying a total cell fluorescent label and a dead cell fluorescent label is a dead effector cell.

4. The method of claim 2, wherein the co-culture sample is obtained by operations including:

obtaining a co-culture product by co-culturing the target cells carrying preset fluorescent labels and the effector cells carrying no fluorescent labels;

marking the co-culture product with dead cell fluorescent labels after co-culturing the target cells and the effector cells for a predetermined time to obtain the co-culture sample, wherein among the plurality of objects in the fixed area of the co-culture sample, an object only carrying a preset fluorescent label is a living target cell, an object carrying a preset fluorescent label and a dead cell fluorescent label is a dead target cell, an object without the fluorescent labels is a living effector cell, and an object only carrying a dead cell fluorescent label is a dead effector cell.

5. The method of claim 1, wherein among the plurality of objects, objects with different cell properties have different image-identifiable features, and the image-identifiable features include a fluorescent label feature and a cell diameter feature.

6. The method of claim 5, wherein the co-culture sample is obtained by operations including:

obtaining a co-culture product by co-culturing the target cells carrying preset fluorescent labels and the effector cells carrying no fluorescent labels;

marking the co-culture product with dead cell fluorescent labels after co-culturing the target cells and the effector cells for a predetermined time to obtain the co-culture sample, wherein among the plurality of objects in the fixed area of the co-culture sample, an object without fluorescent labels and having a diameter greater than or equal to a minimum diameter of the target cells is a living target cell, an object carrying a dead cell fluorescent label and having a diameter greater than or equal to the minimum diameter of the target cells is a dead target cell, an object without fluorescent labels and having a diameter smaller than a maximum diameter of the effector cells is a living effector cell, and an object carrying a dead cell fluorescent label and having a diameter smaller than the maximum diameter of the effector cells is a dead effector cell.

7. The method of claim 1, wherein the cell parameters include at least one first cell parameter associated with the cell properties of the plurality of objects, the at least one first cell parameter including one or more of a total count of the target cells and the effector cells, a total count of the target cells, a total count of the living target cells, a total count of the dead target cells, a death rate of the target cells, a total count of the effector cells, a total count of the living effector cells, a total count of the dead effector cells, and a death rate of the effector cells.

8. The method of claim 7, wherein evaluating at least one of the cell-killing efficacy or the immune activity of the effector cells based on the cell parameters comprises:

comparing the death rate of the target cells with a death rate threshold to obtain a comparison result, and evaluating at least one of the cell-killing efficacy or the immune activity of the effector cells according to the comparison result, wherein the death rate threshold includes an upper limit and a lower limit.

9. The method of claim 8, wherein the evaluating at least one of the cell-killing efficacy or the immune activity of the effector cells according to the comparison result includes:

in response to the comparison result indicating the death rate of the target cells is higher than the upper limit of the death rate threshold, determining that the at least one of the cell-killing efficacy or the immune activity of the effector cells is higher than a normal level;

in response to the comparison result indicating the death rate of the target cells is between the upper and lower limits of the death rate threshold, determining that the at least one of the cell-killing efficacy or the immune activity of the effector cells is at the normal level; or in response to the comparison result indicating the death rate of the target cells is lower than the lower limit of the death rate threshold, determining that the at least one of the cell-killing efficacy or the immune activity of the effector cells is lower than the normal level.

10. The method of claim 1, wherein the method further comprises:

obtaining a plurality of control group microscopic images of a fixed area of a target cell sample of a control group, wherein the target cell sample of the control group is obtained by culturing the target cells alone, and the fixed area of the target cell sample of the control group includes a plurality of first-control objects with the image-identifiable features; and performing an image overlapping synthesis analysis based on the plurality of control group microscopic images to obtain the cell properties of the plurality of first-control objects, and make statistics to the cell parameters associated with the cell properties.

11. The method of claim 1, wherein the method further comprises:

obtaining a plurality of control group microscopic images of a fixed area of an effector cell sample of the control group, wherein the effector cell sample of the control group is obtained by culturing the effector cells alone, and the fixed area of the effector cell sample of the control group includes a plurality of control objects with the image-identifiable features; and performing an image overlapping synthesis analysis based on the plurality of microscopic images of the control group to obtain cell properties of the plurality of control objects and make statistics to the cell parameters associated with the cell properties.

12. The method of claim 1, wherein extracting, in each of the plurality of microscopic images, a plurality of object regions and corresponding contour information comprises:

performing a filtering processing based on each of the plurality of microscopic images to obtain a plurality of denoised microscopic images;

performing a binarization processing based on each of the plurality of denoised microscopic images to obtain a plurality of binarized microscopic images; and performing a segmentation of the plurality of objects based on each of the plurality of binarized microscopic images to extract the plurality of object regions and the corresponding contour information.

13. The method of claim 1, wherein the performing, for the plurality of microscopic images, an object overlapping determination based on the plurality of object regions and the corresponding contour information to obtain an overlapping determination result includes:

obtaining the overlapping determination result by, for each object region of the plurality of object regions in each microscopic image of the plurality of microscopic images, traversing each of the other object regions of the other microscopic images to perform the object overlapping determination, wherein in an object overlapping determination process:

if two object regions that are being compared are determined to be overlapping in the primary overlapping determination, a determination result of the primary overlapping determination is designated as the overlapping determination result of the object overlapping determination; and if the two object regions that are being compared are determined not to be overlapping in the primary overlapping determination, performing the secondary overlapping determination based on the two object regions that are being compared, and a determination result of the secondary overlapping determination is designated as the overlapping determination result of the object overlapping determination.

14. The method of claim 13, wherein the primary overlapping determination further includes:

determining the feature points and feature point coordinates of the two object regions based on the contour information corresponding to the two object regions to be determined, wherein the two object regions are located on different microscopic images, respectively;

calculating a feature point coordinate distance of the two object regions;

comparing the feature point coordinate distance with a preset distance threshold; and determining whether the two object regions overlap by:

in response to determining that the feature point coordinate distance of the two object regions is less than or equal to the distance threshold, determining that the two object regions overlap; or in response to determining that the feature point coordinate distance of the two object regions is greater than the distance threshold, determining that the two object regions do not overlap.

15. The method of claim 13, wherein the secondary overlapping determination further includes:

calculating the intersection-union ratio of the plurality of object regions based on the two object regions to be determined;

comparing the intersection-union ratio of the plurality of object regions and a preset intersection ratio threshold; and in response to determining that the intersection-union ratio of the plurality of object regions is greater than or equal to the intersection ratio threshold, determining that the two object regions overlap; or in response to determining that the intersection-union ratio of the plurality of object regions is less than the intersection ratio threshold, determining that the two object regions do not overlap.

16. The method of claim 1, wherein the obtaining the cell properties of the plurality of objects and make statistics to cell parameters associated with the cell properties further includes:

extracting at least one fusion feature point in each of the plurality of microscopic images;

registering the plurality of microscopic images based on the corresponding fusion feature points of the plurality of microscopic images to obtain a plurality of registered microscopic images;

obtaining a fused image by fusing the plurality of registered microscopic images based on at least one of a transparency or a chroma; and analyzing the fused image to obtain the cell properties of the plurality of objects and make statistics to the cell parameters associated with the cell properties.

17. The method of claim 16, wherein the analyzing the fused image to obtain the cell properties of the plurality of objects and make statistics to the cell parameters associated with the cell properties includes:

processing the fused image based on an image recognition model to obtain the cell properties of the plurality of objects and make statistics to the cell parameters associated with the cell properties, the image recognition model being a machine-learning model.

18. The method of claim 16, wherein the analyzing the fused image to obtain the cell properties of the plurality of objects and make statistics to the cell parameters associated with the cell properties includes:

obtaining a plurality of object image blocks based on the fused image;

extracting color features and shape features in the plurality of object image blocks; and obtaining, based on the color features and the shape features of the plurality of object image blocks, the cell properties of the plurality of the objects, and make statistics to the cell parameters associated with the cell properties.

* * * * *